United States Patent
Ohshima et al.

(10) Patent No.: US 6,395,738 B1
(45) Date of Patent: May 28, 2002

(54) BENZOFURAN DERIVATIVES

(75) Inventors: Etsuo Ohshima, Nagareyama; Tohru Matsuzaki; Haruhiko Manabe, both of Shizuoka, all of (JP)

(73) Assignee: Kyowa Hakko Kogyo Co., Ltd., Tokyo (JP)

(*) Notice: Subject to any disclaimer, the term of this patent is extended or adjusted under 35 U.S.C. 154(b) by 0 days.

(21) Appl. No.: 09/509,485

(22) PCT Filed: Oct. 1, 1998

(86) PCT No.: PCT/JP98/04430

§ 371 (c)(1),
(2), (4) Date: Mar. 29, 2000

(87) PCT Pub. No.: WO99/16768

PCT Pub. Date: Apr. 8, 1999

(30) Foreign Application Priority Data

| Oct. 1, 1997 | (JP) | 9-268399 |
| Feb. 6, 1998 | (JP) | 10-25364 |
| May 27, 1998 | (JP) | 10-145220 |
| May 28, 1998 | (JP) | 10-146738 |

(51) Int. Cl.$^7$ ............ A61K 31/495; A61K 31/34; C07D 241/04; C07D 405/00; C07D 307/87
(52) U.S. Cl. ............ 514/252.13; 514/254.1; 514/255.05; 514/469; 544/358; 544/376; 544/386; 544/398; 544/399; 546/281.7; 546/284.1; 549/462; 549/467; 549/468
(58) Field of Search .......... 514/252.13, 254.1, 514/255.05, 469; 544/358, 386, 376, 398, 399; 546/281.7, 284.1; 549/462, 467, 468

(56) References Cited

U.S. PATENT DOCUMENTS

| 5,773,467 A | 6/1998 | Dyke et al. ............ 514/469 |
| 5,965,574 A | 10/1999 | Chen et al. ............ 514/320 |
| 5,972,936 A | * 10/1999 | Dyke et al. ............ 514/233.4 |

FOREIGN PATENT DOCUMENTS

| DE | 2157424 | * 7/1991 |
| EP | 943 613 | 9/1999 |
| WO | 9109849 | * 7/1991 |
| WO | 771 794 | 5/1997 |
| WO | 97/20833 | 6/1997 |
| WO | WO 97/44337 | 11/1997 |

OTHER PUBLICATIONS

J. Med. Chem., "Novel Selective PDE IV Inhibitors as Antiasthmatic Agents", vol. 39, pp. 2696–2704 (1996).
J. Allergy Clin. Immunol., S444 (1997).
The Journal of Pharmacology And Experimental Therapeutics, "Inhibition of Type IV Phosphodiesterase by . . . ", vol. 278, No. 1, pp. 37–41 (1996).
European Journal of Pharmacology, "Ameliorating effects of rolipram on . . . ", vol. 321 (1997), pp. 273–278.
European Journal of Pharmacology, "Rolipram, a cyclic AMP–selective phosphodiesterase . . . ", vol. 272 (1995), pp. 107–110.
Nature Medicine, "The antidepressant rolipram suppresses cytokine . . . ", vol. 1, No. 3 (1995), pp. 244–248.
Clin Exp Immunol, "Anti–inflammatory activity of phosphodiesterase . . . ", vol. 100 (1995), pp. 126–132.
The Journal of Investigative Dermatalogy, "Ro 20–1724: An Agent that Significantly Improves Psoriatic Lesions . . . ", vol. 73, No. 4 (1979), pp. 261–263.
International Clinical Psychopharmacology, "Rolipram versus Imipramine in Inpatients with Major . . . ", vol. 3 (1988), pp. 245–253.
Molecular Brain Research, "Alterations of cAMP response element–binding activity . . . ", vol. 41 (1996), pp. 210–215.
AIDS, Rapid Science Publishers, "Rolipram, a specific type IV phosphodiesterase inhibitor . . . ", vol. 9, No. 10 (1995), pp. 1137–1144.
Diabetes, "The Phosphodiesterase Inhibitors Pentoxifylline and Rolipram . . . ", vol. 47, (1998), pp. 570–575.
Exp. Opin. Invest., "The therapeutic potential of PDE4 inhibitors", vol. 8, No. 9 (1999), pp. 1301–1325.

* cited by examiner

Primary Examiner—Richard L. Raymond
Assistant Examiner—Sudhaker B. Patel
(74) Attorney, Agent, or Firm—Fitzpatrick, Cella, Harper & Scinto

(57) ABSTRACT

The present invention relates to benzofuran derivatives represented by following general formula (I):

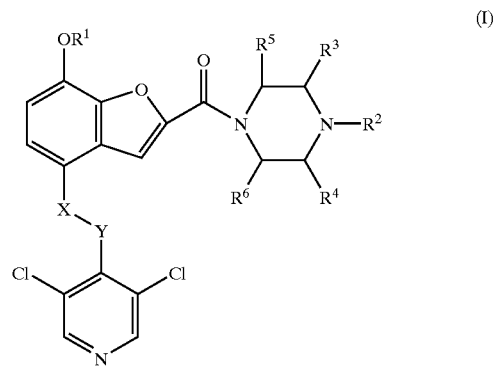

wherein $R^1$ represents lower alkyl, $R^2$ represents hydrogen or substituted or unsubstituted lower alkyl, $R^3$, $R^4$, $R^5$ and $R^6$ independently represent hydrogen or lower alkyl, X represents $CH_2$ or C=O, and Y represents $CH_2$ or NH, or pharmaceutically acceptable salts thereof.

8 Claims, No Drawings

BENZOFURAN DERIVATIVES

FIELD OF THE INVENTION

The present invention relates to benzofuran derivatives which have phosphodiesterase (PDE) IV inhibitory activity and which are useful as a therapeutic agent for inflammatory allergic diseases such as bronchial asthma, allergic rhinitis and nephritis; autoimmune diseases such as rheumatism, multiple sclerosis, Crohn's diseases, psoriasis and systemic lupus erythematosus; diseases of the central nervous system such as depression, amnesia and dementia; organopathy associated with ischemic reflux caused by cardiac failure, shock and cerebrovascular disease, and the like; insulin-resistant diabetes; wounds; AIDS; and the like.

BACKGROUND ART

Heretofore, it is known that the functions of numerous hormones and neurotransmitters are expressed by an increase in the concentration of adenosine 3',5'-cyclic monophosphate (cAMP) or guanosine 3',5'-cyclic monophosphate (cGMP), both of which are the secondary messengers in cells. The cellular concentrations of cAMP and cGMP are controlled by the generation and decomposition thereof, and their decomposition is carried out by PDE. Therefore, when PDE is inhibited, the concentrations of these secondary cellular messengers increase. Up to the present, 7 kinds of PDE isozymes have been found, and the isozyme-selective PDE inhibitors are expected to exhibit pharmaceutical effect based on their physiological significance and distribution in vivo [TiPS, 11, 150 (1990), ibid., 12, 19 (1991)].

It is known that the activation of inflammatory leukocytes can be suppressed by increasing the concentration of the cellular cAMP. The extraordinary activation of leukocytes causes secretion of inflammatory cytokines such as tumor necrosis factor (TNF), and expression of the cellular adhesion molecules such as intercellular adhesion molecules (ICAM), followed by cellular infiltration [J. Mol. Cell. Cardiol., 12 (Suppl. II), S61 (1989)].

It is known that the contraction of a respiratory smooth muscle can be suppressed by increasing the concentration of the cellular cAMP (T. J. Torphy in Directions for New Anti-Asthma Drugs, eds S. R. O'Donell and C. G. A. Persson, 1988, 37, Birkhauser-Verlag). The extraordinary contraction of a respiratory smooth muscle is a main symptom of bronchial asthma. Infiltration of inflammatory-leukocytes such as neutrophils is observed in lesions of organopathy associated with ischemic reflux such as myocardial ischemia. It has been found that the type IV PDE (PDE IV) mainly participates in the decomposition of cAMP in these inflammatory cells and tracheal smooth muscle cells. Therefore, the inhibitors selective for PDE IV are expected to have therapeutic and/or preventive effect on inflammatory diseases, respiratory obstructive diseases, and ischemic diseases.

Further, the PDE IV inhibitors are expected to prevent the progress and spread of the inflammatory reaction transmitted by inflammatory cytokines such as TNFα and interleukin (IL)-8, because the PDE IV inhibitors suppress the secretion of these cytokines by increasing the concentration of cAMP. For example, TNFα is reported to be a factor of insulin-resistant diabetes because it declines the phosphorylating mechanism of insulin receptors in muscle and fat cells [J. Clin. Invest., 94, 1543 (1994)]. Similarly, it is suggested that the PDE IV inhibitors may be useful for autoimmune diseases such as rheumatoid arthritis, multiple sclerosis, and Crohn's disease because TNFα participates in the onset and progress of these diseases [Nature Medicine, 1, 211 (1995) and ibid., 1, 244 (1995)].

WO97/20833 discloses benzofurancarboxamide derivatives having PDE IV inhibitory activity, but none of compounds having substituted piperazinylcarbonyl bound at the 2-position of the benzofuran ring are specifically disclosed.

WO96/36624 discloses benzofuran derivatives having PDE IV inhibitory activity.

However, the conventional PDE IV inhibitors have a problem of induction of vomiting [TiPS, 18, 164 (1997)].

DISCLOSURE OF THE INVENTION

A novel and useful PDE IV inhibitor is expected to have prophylactic or therapeutic effects on a wide variety of diseases. An object of the present invention is to provide benzofuran derivatives having a superior anti-inflammatory activity and causing no vomiting.

The present invention relates to benzofuran derivatives represented by following formula (I):

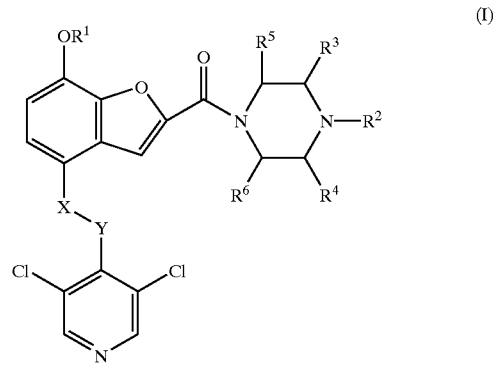

wherein $R^1$ represents lower alkyl, $R^2$ represents hydrogen or substituted or unsubstituted lower alkyl, $R^3$, $R^4$, $R^5$ and $R^6$ independently represent hydrogen or lower alkyl, X represents $CH_2$ or C=O, and Y represents $CH_2$ or NH, or pharmaceutically acceptable salts thereof.

Hereinafter, the compounds represented by the general formula (I) are referred to as Compound (I). The same applies to the compounds of other formula numbers.

In addition, the present invention relates to a therapeutic agent for inflammatory allergic diseases, which comprises Compound (I) or a pharmaceutically acceptable salt thereof as an active ingredient.

Further, the present invention relates to a method for treating inflammatory allergic diseases, which comprises administering an effective amount of Compound (I) or a pharmaceutically acceptable salt thereof.

Furthermore, the present invention relates to a use of Compound (I) or a pharmaceutically acceptable salt thereof for the preparation of a pharmaceutical composition which is useful for the treatment of inflammatory allergic diseases.

The pharmaceutically acceptable acid addition salt of Compound (I) includes inorganic acid salts such as hydrochloride, sulfate, nitrate and phosphate, and organic acid salts such as acetate, maleate, fumarate and citrate.

In the definitions of the groups in formula (I), the lower alkyl includes straight-chain or branched $C_1$ to $C_8$ alkyl groups such as methyl, ethyl, propyl, isopropyl, butyl, sec-butyl, tert-butyl, pentyl, hexyl, heptyl and octyl.

The substituted lower alkyl has the same or different 1 to 3 substituents such as hydroxy and substituted or unsubstituted lower alkoxy. The alkyl moiety of the lower alkoxy has the same meaning as the lower alkyl defined above, and the substituted lower alkoxy has the same or different 1 to 3 substituents such as hydroxy.

Among Compound (I), preferred compounds are Compound (I) wherein $R^2$ is substituted or unsubstituted lower alkyl, and specifically preferred compounds are Compound (I) wherein $R^2$ is lower alkyl or hydroxy-substituted lower alkyl.

Among Compound (I), preferred compounds are Compound (I) wherein X is $CH_2$, and Y is $CH_2$; or x is C=O, and Y is $CH_2$ or NH.

A process for producing Compound (I) is described below.

Process: Compound (I) can be produced according to the following processes.

Process 1

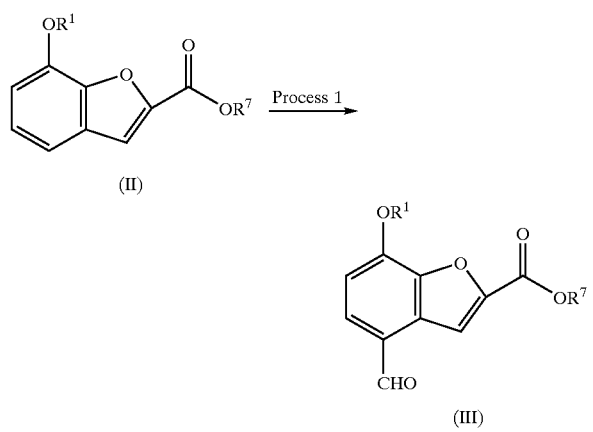

(In the formulae, $R^1$ has the same meaning as defined above, and $R^7$ represents lower alkyl.)

In the above formulae, the lower alkyl represented by $R^7$ has the same meaning as the lower alkyl defined above.

Compound (III) can be produced by subjecting Compound (II) to formylation. Compound (II) as the starting material can be synthesized according to a method described in Bull. Soc. Chim. Fr., 2355 (1973) or a similar method thereto.

Specifically, Compound (III) can be obtained by reacting Compound (II) in an inert solvent with 1 equivalent to a large excess of dichloromethyl methyl ether in the presence of 1 equivalent to an excess of an acid for 5 minutes to 48 hours at a temperature between −50° C. and the boiling point of the solvent used.

Examples of the acid are methanesulfonic acid, hydrochloric acid, sulfuric acid, trifluoroacetic acid, boron trifluoride, aluminum chloride, stannic chloride, titanium tetrachloride, zinc chloride and ferric chloride, among which titanium tetrachloride is preferable.

Examples of the inert solvent are tetrahydrofuran (THF), dioxane, diethyl ether, ethylene glycol, triethylene glycol, glime, diglime, dichloromethane, chloroform, benzene and toluene, among which halogenated hydrocarbons such as dichloromethane and chloroform are preferable.

Processes 2 to 4

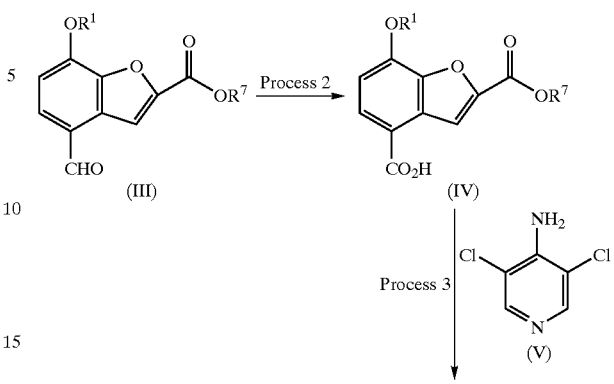

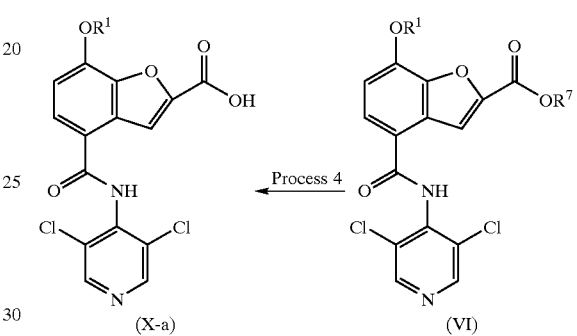

(In the formulae, $R^1$ and $R^7$ have the same meanings as defined above.)

Process 2: Compound (IV) is obtained by oxidation of Compound (III). For oxidation of the aldehyde to its corresponding carboxylic acid, a method for oxidation with metal oxidizing agents (permanganate, chromic acid) and a method for oxidation with halides (halogenous acid, hypohalogenous acid, salts thereof) are known (see *Jikken Kagaku Koza*, 4th edition, 23 (1990), Maruzen). Hereinafter, an example of reaction by sodium chlorite (J. Org. Chem., 51, 567 (1986)) is described. Compound (IV) can be obtained by reacting Compound (III) with 1 equivalent to an excess of sodium chlorite at a temperature between 0° C. and 30° C. for 1 to 48 hours in the presence of 1 equivalent to an excess of sulfamic acid in aqueous acetic acid.

Process 3: Compound (VI) can be obtained by dehydration condensation reaction between Compound (IV) and Amine Compound (V). Compound (IV) is converted into its corresponding acid chloride by treating it with 1 equivalent to a large excess of thionyl chloride in an inert solvent, if necessary in the presence of a catalytic amount to an excess of a base, for 30 minutes to 10 hours at a temperature between room temperature and the boiling point of the solvent used, and said acid chloride is reacted without isolation with 1 equivalent to an excess of Amine Compound (V) in an inert solvent in the presence of 1 equivalent to an excess of a base for 5 minutes to 10 hours at a temperature between −80° C. and the boiling point of the solvent used, whereby Compound (VI) can be obtained. If necessary, said acid chloride as a reaction intermediate may be isolated. Alternatively, mixed acid anhydrides corresponding to Compound (IV) may be produced by using ethyl chloroformate etc. in place of thionyl chloride in the reaction described above, followed by reaction with Amine Compound (V), whereby Compound (VI) can also be obtained.

Examples of the base are sodium hydroxide, potassium hydroxide, sodium methoxide, potassium ethoxide, sodium hydride, potassium hydride, butyl lithium, lithium diisopropylamide (LDA), potassium tert-butoxide, triethylamine, diisopropylethylamine, tributylamine, dicyclohexylmethylamine, N-methylmorpholine, N-methylpiperidine, diazabicycloundecene (DBU) and diazabicyclononene(DBN).

Examples of the inert solvent are THF, dioxane, diethyl ether, ethylene glycol, triethylene glycol, glime, diglime, methanol, ethanol, butanol, isopropanol, dichloromethane, chloroform, benzene, toluene, dimethylformamide (DMF) and dimethyl sulfoxide (DMSO).

Process 4: Compound (X-a) can be obtained by reacting Compound (VI) in an inert solvent with 1 equivalent to a large excess of an aqueous alkali solution for 5 minutes to 10 hours at a temperature between 0° C. and the boiling point of the solvent used.

Examples of the aqueous alkali solution are aqueous solutions of sodium hydroxide or potassium hydroxide, and examples of the inert solvent are dioxane, methanol and THF.

Processes 5 to 9

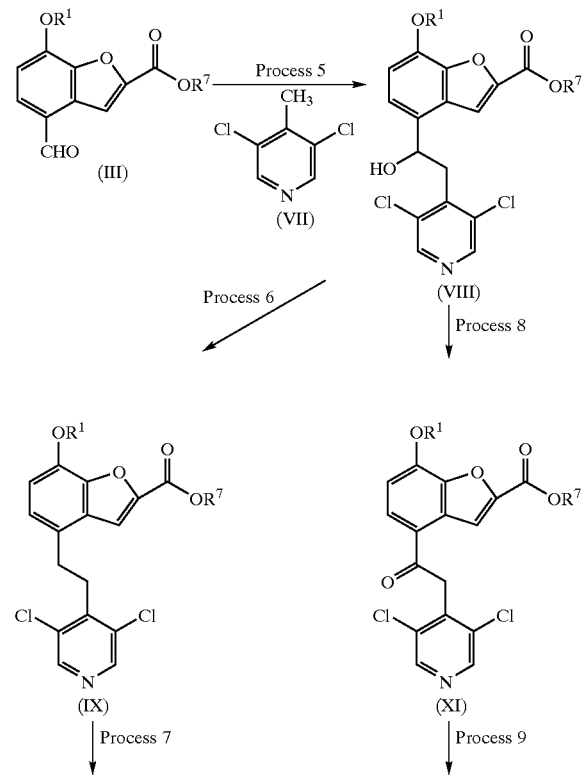

-continued

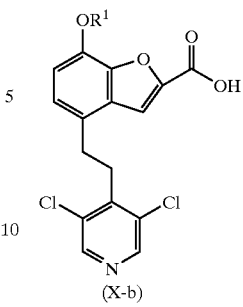
(X-b)

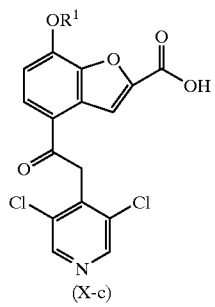
(X-c)

(in the formulae, $R^1$ and $R^7$ have the same meanings as defined above.)

Process 5: Compound (VIII) can be obtained by addition reaction of Compound (III) obtained in Process 1 and Compound (VII). Compound (VII) is treated in an inert solvent with 1 equivalent to a large excess of a base for 5 minutes to 10 hours at a temperature between –100° C. and the boiling point of the solvent used, and then reacted with Compound (III) for 5 minutes to 30 hours at a temperature between –100° C. and the boiling point of the solvent used, whereby Compound (VIII) can be obtained. Compound (VII) can be synthesized by a method described in e.g. Handbook for Experimental Methods in Organic Synthesis (compiled by Society of Synthetic Organic Chemistry, Japan), page 577, 1990.

Examples of the base are sodium hydroxide, potassium hydroxide, sodium methoxide, potassium ethoxide, sodium hydride, potassium hydride, butyl lithium, LDA, potassium tert-butoxide, triethylamine, diisopropylethylamine, tributylamine, dicyclohexylmethylamine, N-methylmorpholine, N-methylpiperidine, DBU and DBN.

Examples of the inert solvent are THF, dioxane, diethyl ether, ethylene glycol, triethylene glycol, glime, diglime, methanol, ethanol, butanol, isopropanol, dichloromethane, chloroform, benzene, toluene, DMF and DMSO.

Process 6: Compound (IX) can be obtained by reduction of Compound (VIII) with hydrosilane. The reduction of a hydroxyl group by a combination of hydrosilane and an acid is well-known (see *Jikken Kagaku Koza*, 4th edition, 26, 197 (1990), Maruzen), and this technique can be used. For example, Compound (VIII) is reacted with 1 equivalent to a large excess of hydrosilane in an inert solvent, more preferably in a halogen-type solvent such as dichloromethane, in the presence of 1 equivalent to an excess of an acid, more preferably in the presence of boron trifluoride for 5 minutes to 48 hours at a temperature between –100° C. and the boiling point of the solvent used, whereby the desired compound (IX) can be obtained.

Examples of the inert solvent are THF, dioxane, diethyl ether, dichloromethane, chloroform, dichloroethane, DMF and DMSO.

Examples of the hydrosilane are triethylsilane, trichlorosilane, n-butylsilane, diphenylsilane, phenylsilane, dimethylphenylsilane, and triethoxysilane.

Examples of the acid are boron trifluoride, titanium tetrachloride, aluminum trichloride, zinc chloride and trifluoroacetic acid.

Process 7: Compound (X-b) can be obtained by treating Compound (IX) according to the same process as in Process 4 above.

Process 8: Compound (XI) can be obtained by reacting Compound (VIII) with 1 equivalent to an excess of an oxidizing agent in an inert solvent including water for 5 minutes to 72 hours at a temperature between 0° C. and the boiling point of the solvent used.

Examples of the oxidizing agent are manganese dioxide, potassium permanganate, pyridinium chlorochromate (PCC) and pyridinium dichromate (PDC).

Examples of the inert solvent are THF, dioxane, diethyl ether, ethylene glycol, triethylene glycol, glime, diglime, acetone, methyl vinyl ketone, dichloromethane, chloroform, benzene, toluene, DMF and DMSO.

Process 9: Compound (X-c) can be obtained by treating Compound (XI) according to the same process as in Process 4 above. Process 10 [Production of Compound (I) wherein X is $CH_2$ and Y is $CH_2$; or X is $C=O$ and Y is NH or $CH_2$]

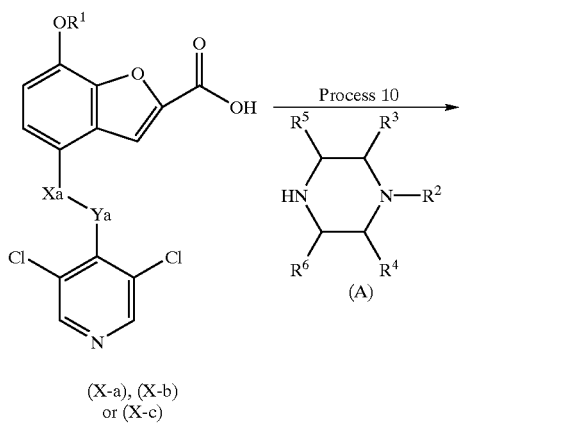

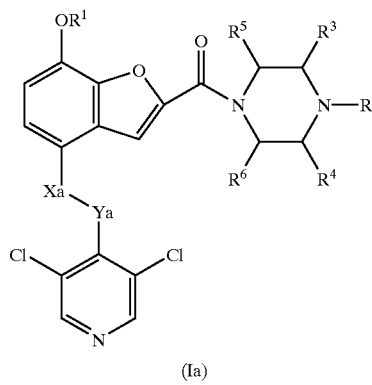

(In the formulae, $R^1$, $R^2$, $R^3$, $R^4$, $R^5$ and $R^6$ have the same meanings as defined above, Xa represents $CH_2$ or $C=O$, and Ya represents $CH_2$ or NH, provided that Ya is not NH when Xa is $CH_2$.)

Compound (Ia) can be obtained by reacting Compound (X-a), (X-b) or (X-c) with Compound (A) in the presence of 1 equivalent to an excess of a condensation agent in an inert solvent at –80 to 50° C. for 5 minutes to 30 hours. If necessary, 1 equivalent to an excess of N-hydroxysuccinimide, 1-hydroxybenzotriazole or 3-hydroxy-4-oxo-3,4-dihydro-1,2,3-benzotriazine may be added.

Examples of the condensation agent are dicyclohexyl carbodiimide, diisopropylcarbodiimide, N-ethyl-N'-3-dimethylaminopropylcarbodiimide and a hydrochloride thereof, benzotriazol-1-yl-tris(dimethylamino)phosphonium hexafluorophosphate and diphenylphosphorylazide.

Examples of the inert solvent are THF, dioxane, diethyl ether, dichloromethane, chloroform, dichloroethane, DMF, DMSO and water.

Compound (A) is commercially available but may be obtained by synthesis. For example, Compound (A) wherein $R^2$ is lower alkyl substituted with hydroxy can be synthesized by the following processes.
Processes 11 to 13

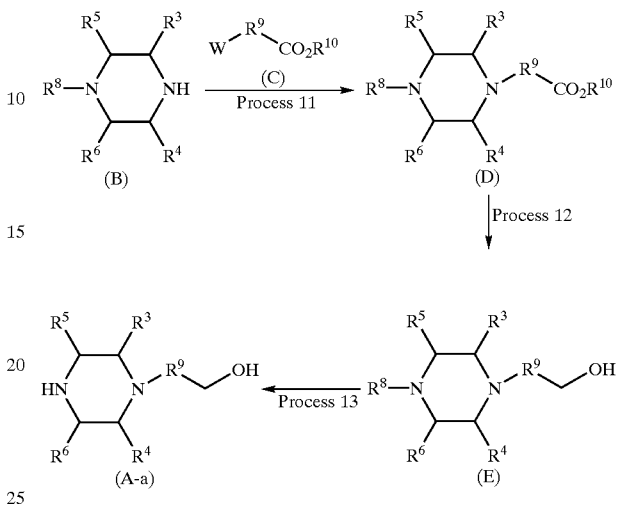

(In the formulae, $R^3$, $R^4$, $R^5$ and $R^6$ have the same meanings as defined above, $R^8$ represents a protective group for an amine, $R^9$ represents lower alkylene, $R^{10}$ represents lower alkyl, and W represents halogen.)

The protective group $R^8$ for an amine includes triphenylmethyl, tert-butoxycarbonyl (Boc), benzyloxycarbonyl and 9-fluorenylmethyloxycarbonyl (Fmoc). The halogen includes a fluorine, chlorine, bromine and iodine atom. The lower alkylene represented by $R^9$ includes straight-chain or branched $C_1$ to $C_7$ alkylene such as methylene, ethylene, propylene, butylene, pentylene and hexylene. The lower alkyl represented by $R^{10}$ has the same meaning as defined above.

Process 11: Synthesis of Compound (D)

Compound (D) can be obtained by reacting Compound (B) with Compound (C) in an inert solvent in the presence of 1 equivalent to a large excess of a base for 5 minutes to 10 hours at a temperature between 0° C. and the boiling point of the solvent used.

Examples of the base are sodium hydroxide, potassium hydroxide, sodium methoxide, potassium ethoxide, sodium hydride, potassium hydride, butyl lithium, LDA, potassium tert-butoxide, triethylamine, diisopropylethylamine, tributylamine, dicyclohexylmethylamine, N-methylmorpholine, N-methylpiperidine, DBU and DBN.

Examples of the inert solvent are THF, dioxane, diethyl ether, ethylene glycol, triethylene glycol, glime, diglime, methanol, ethanol, butanol, isopropanol, dichloromethane, chloroform, benzene, toluene, DMF and DMSO.

Compounds (B) and (C) are commercially available.
Process 12: Synthesis of Compound (E)

Compound (E) can be obtained by reducing Compound (D). Compound (E) can be obtained by treating Compound (D) in an inert solvent with 1 equivalent to a large excess of a reducing agent for 5 minutes to 10 hours at a temperature between 0° C. and the boiling point of the solvent used.

Examples of the reducing agent are sodium borohydride, lithium borohydride, lithium aluminum hydride and diisobutylaluminum hydride.

Examples of the inert solvent are THF, dioxane, diethyl ether, ethylene glycol, triethylene glycol, glime, diglime, methanol, ethanol, butanol, isopropanol, dichloromethane, chloroform, benzene, toluene, DMF and DMSO.

Process 13: Synthesis of Compound (A-a)

Compound (A-a) can be obtained by subjecting Compound (E) to suitable de-protection conditions.

For example, when $R^8$ is a protective group such as tert-butoxycarbonyl or triphenylmethyl capable of being eliminated under acidic conditions, the desired compound can be obtained by reacting Compound (E) in an inert solvent with 1 equivalent to a large excess of an acidic solution as the acid for 5 minutes to 10 hours at a temperature between 0° C. and the boiling point of the solvent used.

Examples of the acidic solution are hydrochloric acid, solutions of hydrogen chloride in ethyl acetate or in dioxane, trifluoroacetic acid and acetic acid.

Examples of the inert solvent are THF, dioxane, diethyl ether, ethylene glycol, triethylene glycol, glime, diglime, methanol, ethanol, butanol, isopropanol, dichloromethane, chloroform, benzene, toluene, DMF and DMSO.

Further, Compound (A) wherein $R^2$ is lower alkoxyalkyl substituted with hydroxy can also be synthesized according to the same method as described above.

Alternatively, Compound (I) can also be produced in the method described below.

Processes 14 and 15 [Production of Compound (I) wherein X is CH$_2$ and Y is CH$_2$; or X is C=O and Y is NH or CH$_2$]

(in the formulae, $R^1$, $R^3$, $R^4$, $R^5$, $R^6$, Xa and Ya have the same meanings as defined above, Z represents halogen, and $R^{2a}$ represents the same groups other than hydrogen as those of $R^2$ defined above.)

In the formulae, the halogen defined as Z includes the same halogen as defied above.

Process 14: Compound (Iaa) can be produced by reacting Compound (X-a), (X-b) or (X-c) with Compound (B) according to the same process as Process 10 described above.

Process 15: Compound (Iab) can be obtained by reacting Compound (Iaa) with Compound (F) in an inert solvent in the presence of 1 equivalent to a large excess of a base for 5 minutes to 10 hours at a temperature between 0° C. and the boiling point of the solvent used.

Examples of the inert solvent are THF, dioxane, diethyl ether, acetone, methyl vinyl ketone, dichloromethane, chloroform, benzene, toluene, DMF and DMSO.

Examples of the base are sodium hydroxide, potassium hydroxide, sodium methoxide, potassium ethoxide, sodium hydride, potassium hydride, butyl lithium, LDA, potassium tert-butoxide, triethylamine, diisopropylethylamine, tributylamine, dicyclohexylmethylamine, N-methylmorpholine, N-methylpiperidine, DBU and DBN.

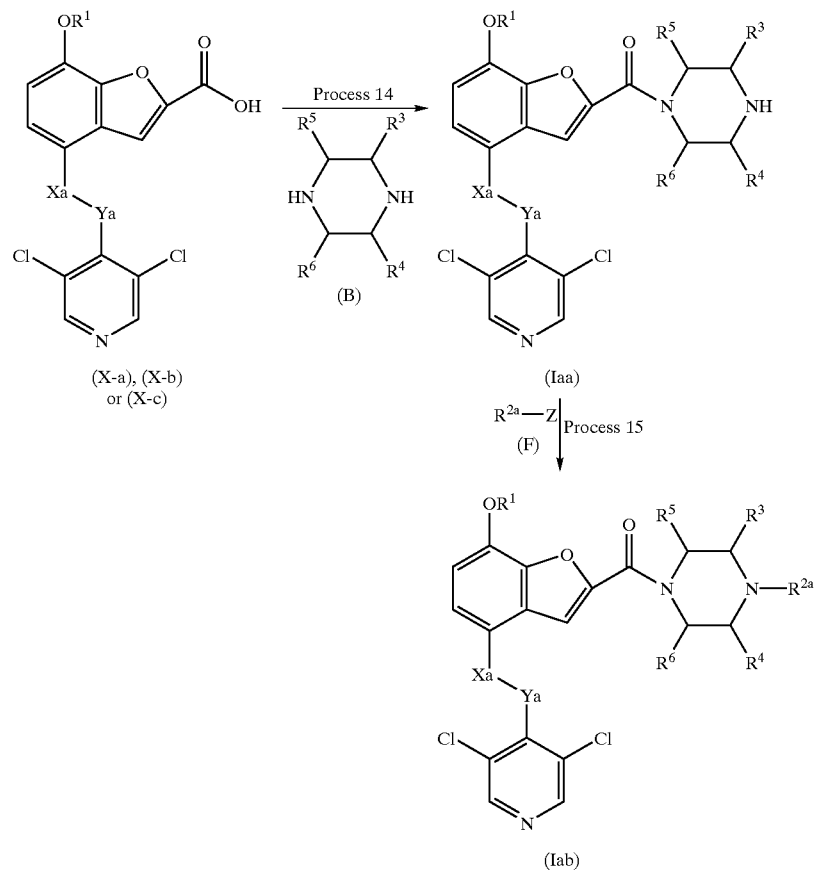

Processes 16 and 17 [Production of Compound (I) wherein X is CH$_2$ and Y is NH]

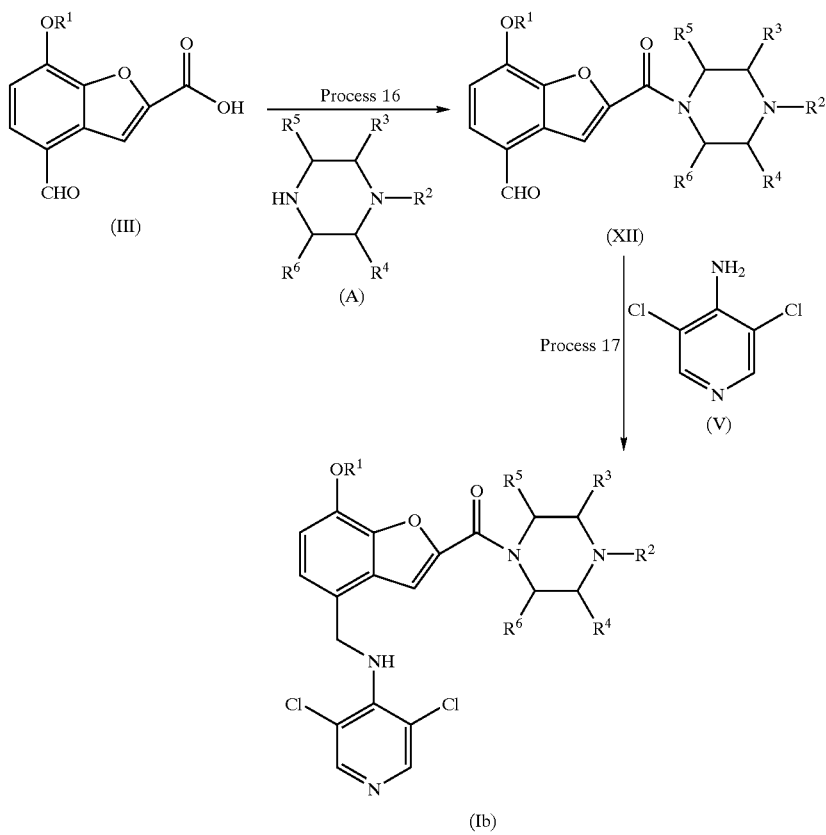

(In the formulae, R$^1$, R$^2$, R$^3$, R$^4$, R$^5$ and R$^6$ have the same meanings as defined above.

Process 16: Compound (XII) can be produced by reacting Compound (III) with Compound (A) according to the same process as Process described above.

Process 17: Compound (Ib) can be obtained by reacting Compound (XII) with Compound (V) in an inert solvent for 5 minutes to 10 hours at a temperature between 0° C. and the boiling point of the solvent used, followed by reducing the formed imine with 1 equivalent to a large excess of a reducing agent for 5 minutes to 10 hours at a temperature between 0° C. and the boiling point of the solvent used.

Examples of the reducing agent are sodium borohydride, sodium cyanoborohydride, lithium aluminum hydride and diborane, and further, it is possible to use catalytic reduction with nickel, platinum and palladium carbon as the catalyst.

Examples of the inert solvent are dichloromethane, chloroform, dichloroethane, benzene, toluene, THF, dioxane, diethyl ether, methanol, ethanol, butanol, isopropanol, DMF, DMSO, acetic acid and water.

The intermediates and the desired compounds in the processes described above can be isolated and purified by subjecting them to separation and purification methods conventionally used in synthetic organic chemistry, such as filtration, extraction, washing, drying, concentration, recrystallization and various kinds of chromatography. The intermediates can also be subjected to subsequent reaction without being particularly purified.

When it is desired to obtain a salt of Compound (I), Compound (I) is dissolved or suspended in a suitable solvent, then an acid is added thereto, and the resulting salt may be isolated and purified.

Further, Compound (I) and pharmaceutically acceptable salts thereof can also exist in the form of adducts with water or various solvents, which are also within the scope of the present invention. Compound (I) may exist in the form of stereoisomers such as enantiomers and diastereomeric isomers, and the present invention encompasses these isomers as well as mixtures thereof.

Hereinafter, specific examples of Compound (I) obtained according to the present invention are shown in Table 1.

TABLE 1

| Compound No. | R$^1$ | R$^2$ | R$^3$ | R$^4$ |
|---|---|---|---|---|
| 1 | CH$_3$ | CH$_3$ | H | H |
| 2 | CH$_3$ | (CH$_2$)$_2$OH | H | H |

TABLE 1-continued

| | | | | |
|---|---|---|---|---|
| 3 | CH$_3$ | CH$_2$CH$_3$ | H | H |
| 4 | CH$_3$ | CH(CH$_3$)CH$_2$OH | H | H |
| 5 | CH$_3$ | CH(CH$_2$CH$_3$)CH$_2$OH | H | H |
| 6 | CH$_3$ | (CH$_2$)$_3$OH | H | H |
| 7 | CH$_3$ | (CH$_2$)$_4$OH | H | H |
| 8 | CH$_3$ | CH(CH$_2$OH)$_2$ | H | H |
| 9 | CH$_3$ | (CH$_2$)$_2$O(CH$_2$)$_2$OH | H | H |
| 10 | CH$_3$ | CH$_3$ | CH$_3$ | CH$_3$ |
| 11 | CH$_3$ | (CH$_2$)$_2$OH | CH$_3$ | CH$_3$ |
| 12 | CH$_3$ | H | H | H |
| 29 | CH$_3$ | (CH$_2$)$_3$OH | CH$_3$ | CH$_3$ |

($R^5$ and $R^6$ represent hydrogen)
Compound 3 is monofumarate.

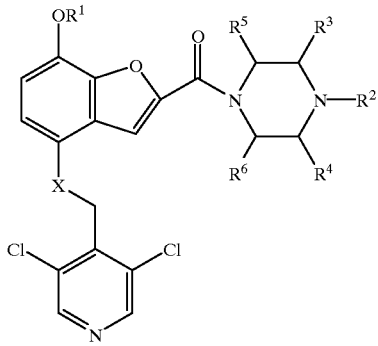

(I)

| Compound No. | X | $R^1$ | $R^2$ | $R^3$ | $R^4$ |
|---|---|---|---|---|---|
| 13 | C=O | CH$_3$ | CH$_3$ | H | H |
| 14 | C=O | CH$_3$ | CH$_2$CH$_2$OH | H | H |
| 15 | C=O | CH$_3$ | CH$_2$CH$_3$ | H | H |
| 16 | C=O | CH$_3$ | CH(CH$_3$)CH$_3$ | H | H |
| 17 | C=O | CH$_3$ | CH$_2$CH$_2$OCH$_2$CH$_3$ | H | H |
| 18 | C=O | CH$_3$ | CH(CH$_3$)CH$_2$OH | H | H |
| 19 | C=O | CH$_3$ | CH(CH$_2$CH$_3$)CH$_2$OH | H | H |
| 20 | C=O | CH$_3$ | (CH$_2$)$_3$OH | H | H |
| 21 | C=O | CH$_3$ | (CH$_2$)$_4$OH | H | H |
| 22 | C=O | CH$_3$ | CH(CH$_2$OH)$_2$ | H | H |
| 23 | C=O | CH$_3$ | (CH$_2$)$_2$O(CH$_2$)$_2$OH | H | H |
| 24 | C=O | CH$_3$ | H | H | H |
| 25 | C=O | CH$_3$ | CH$_3$ | CH$_3$ | CH$_3$ |
| 26 | C=O | CH$_3$ | CH$_2$CH$_2$OH | CH$_3$ | CH$_3$ |
| 27 | CH$_2$ | CH$_3$ | CH$_3$ | H | H |
| 28 | CH$_2$ | CH$_3$ | CH$_2$CH$_2$OH | H | H |
| 30 | C=O | CH$_3$ | (CH$_2$)$_3$OH | CH$_3$ | CH$_3$ |

($R^5$ and $R^6$ represent hydrogen)
Compounds 15, 16, 17, 27 and 30 are monofumarates.
Compound 28 is 0.5 fumarate.
Compound 24 is monohydrochloride.

Hereinafter, the pharmacological activity of typical Compound (I) is described in more detail by reference to the experimental examples.

TEST EXAMPLE 1

Inhibition Test on Recombinant Human PDE IV Enzyme

Human phosphodiesterase cDNA (HSPDE4A) was isolated from testicles. Its predicted amino acid sequence is identical with the sequence (HSPDE4A5) reported by Bolger, G. et al. (Mol. Cell. Biol., 6558 (1993)) except that 223 amino acids have been deleted from the N-terminal thereof. This recombinant protein was expressed by an *E. coli* expression plasmid and then purified. The PDE activity was measured in the following 2-step process according to the method of Kincaid, R. and Manganiello, V. [Method. Enzymol., 159, 457 (1988)]. The substrate used was [$^3$H] cAMP (final concentration: 1 mmol/l), and the reaction was performed in a standard mixture containing N,N-bis(2-hydroxyethyl)-2-aminoethanesulfonic acid (50 mmol/l, pH 7.2), MgCl$_2$ (1 mmol/l) and soybean trypsin inhibitor (0.1 mg/ml). The reaction was initiated by adding the enzyme thereto, and the mixture was incubated at 30° C. for 10 to 30 minutes. The reaction was quenched by hydrochloric acid, and the formed 5'-AMP was completely decomposed with 5'-nucleosidase. This sample was subjected to chromatography on DEAE-Sephadex A-25, and the eluted [$^3$H] adenosine was counted with a scintillation counter. The test compound was added after dissolved (concentration: 1.7%) in DMSO.

The results are shown in Table 2.

TABLE 2

| Compound No. | Ratio of inhibition (%) |
|---|---|
| 1 | 25/75 |
| 2 | 22/72 |
| 3 | 20/71 |
| 4 | 28/85 |
| 5 | 41/89 |
| 6 | 24/81 |
| 7 | 35/83 |
| 9 | 29/78 |
| 10 | 9/75 |
| 11 | 48/88 |

Concentration of Test Compounds: $10^{-8}/10^{-7}$ mol/L

All compounds showed a high inhibitory activity of 70% or more concentration of $10^{-7}$ mol/l.

TEST EXAMPLE 2

Inhibitory Activity on Production of TNF α in Mouse Model with LPS-Induced Sepsis Lipopolysaccharides (LPS, Difco) were dissolved in phsysiological saline at a final concentration of 0.2 mg/ml and administered in a dose of 200 μl/20 g body weight into tail veins of 5 to 6 animals/group (BALB/c male mice (7-week-old) (Nippon Charles River)), and after 1 hour, blood was collected from the eye ground and serum was separated therefrom. The test compound was a dissolved or suspended at a final concentration of 1 mg/ml in a 0.5% methyl cellulose solution/ and 90 minutes before administration of LPS, it was orally administered in a dose of 200 μl/20 g body weight. The concentration of TNF α in the serum was determined by enzyme-linked immunosorbent assay.(ELISA). 4 mg/ml anti-mouse TNF α monoclonal antibody (Genzyme) diluted with phosphate buffered saline (PBS) was added in a volume of 50 μl/well to a 96-well flat-bottom microtiter plate (Nunc Immunoplate "Maxi Sorp", Nunc Ltd.), followed by coating thereof on each well at 4° C. for 12 hours. Then, phosphate buffered saline containing 1% bovine serum albumin (BSA) (1% BSA-PBS) was added thereto in a volume of 200 μl/well and the plates were left at room temperature for 1 hour to block non-specific binding. Thereafter, the plate was washed with phosphate buffered saline, and the test serum diluted 2-fold with 1% BSA-PBS was added in a volume of 100 μl/well and left for 2 hours at room temperature. In addition, recombinant mouse TNF α (Genzyme) diluted with 1% BSA-PBS was treated in the same procedure and used as the standard. These plates were washed 3 times with PBS (0.05% Tween-PBS) containing 0.05% polyoxyethylene sorbitan monolaurate (Tween 20, Wako Ltd.) Then, biotin-labeled anti-mouse TNF α polyclonal antibody (Pharmingen) diluted at a concentration of 1 μg/ml with 1% BSA-PBS was added thereto in a volume of 50 μl/well, and the plates were left at room temperature for 1 hour, and washed 3 times with 0.05% Tween-PBS. Horseradish Peroxidase Avidin D (Vector) diluted 4000-fold with 1% BSA-PBS was added thereto in a volume of 100 μl/well and the plates were left for 30 minutes at room temperature. Finally, these plates were washed 3 times with 0.05% Tween-PBS, and 3,3',5,5'-tetramethylbenzidine was added thereto in a volume of 100 μl/well, and upon coloration, the reaction was quenched by adding 100 μl/well of 10% sulfuric acid to each well. The absorbance at 450 nm was measured. The concentration of TNF α in the serum was calculated from a calibration curve.

The ratio of inhibition of TNFα production by the test compound was determined according to the following equation:

Ratio of inhibition(%)=(A−B)/A    (Equation)

A: Concentration of TNF α in the control.

B: Concentration of TNF α in the sample in the presence of the test compound.

The concentration of TNF α in the control indicates the concentration in the absence of the test compound (a 0.5% methyl cellulose solution alone).

The comparative compounds used were 7-methoxy-4-[1-oxo-2-(4-pyridyl)ethyl]-spiro[2,3-dihydrobenzofuran-2,1'-cyclopentane].hydrochloride (referred to hereinafter as Compound P, JP-A 8-836624, Example 100) shown in formula (P):

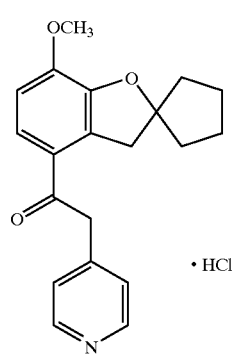

(P)

and 2-benzoyl-4-(3,5-dichloro-4-pyridyl)carbamoyl-7-methoxybenzofuran (referred to hereinafter as Compound Q, JP-A 8-534708, Example 35) shown in formula (Q):

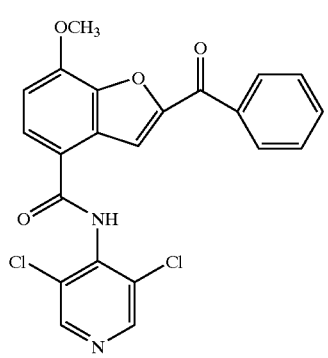

(Q)

The results are shown in Table 3.

TABLE 3

| Compound No. | Dose (mg) | Ratio of inhibition (%) |
|---|---|---|
| 1 | 30 | 68 |
| 2 | 30 | 65 |
| 3 | 30 | 50 |
| 5 | 30 | 53 |
| 6 | 30 | 33 |
| 10 | 30 | 46 |
| 12 | 30 | 27 |
| 13 | 30 | 65 |
| 14 | 30 | 65 |
| 15 | 30 | 61 |
| 16 | 30 | 67 |
| 17 | 30 | 62 |
| 18 | 30 | 66 |
| 19 | 30 | 68 |
| 20 | 30 | 40 |
| 21 | 30 | 28 |
| 22 | 30 | 52 |
| 24 | 30 | 47 |
| 25 | 30 | 53 |
| P | 30 | 81 |
| Q | 30 | 30 |

It is evident from Table 3 that as compared with Compounds P and Q which showed a high inhibitory activity on production of TNF α, Compound (I) exhibited an equivalent inhibitory activity.

TEST EXAMPLE 3

Vomiting Test on Male Sunkus

Male *Sunkus murinus* weighing about 60 g, 5 to 15 animals/group, were used in the test According to the method of Matsuki et al. (Japan J. Pharmacol., 48, 303 (1988)), each Sunkus animal was isolated and left in a wire-netting cage (15 cm width×21 cm length×15 cm height). Each test compound was suspended in physiological saline containing 0.5% Tween 80 and then intraperitoneally (i.p.) administered into each animal in a dose of 10 μl/g. After the test compound was administered, the animals were observed for 1 hour, and the frequency of vomiting was determined. The results were expressed in the number of animals with vomiting/the number of tested animals in the group given the test compound.

Compounds P and Q were used as the comparative compounds.

The results are shown in Table 4.

TABLE 4

| Compound No. | Dose (mg) | Number of animals with vomiting/Number of tested animals |
|---|---|---|
| 1 | 10 | 0/5 |
| 2 | 10 | 0/5 |
| 13 | 10 | 0/5 |
| 14 | 10 | 0/5 |
| P | 10 | 5/5 |
| Q | 10 | 0/5 |

As shown above, all Compounds (I) of the present invention did not permit vomiting as opposed to comparative Compound P which though having a high inhibitory activity on production of TNF α, caused vomiting as a side effect. Compound (I) is a compound having a high inhibitory activity on production of TNF α and simultaneously realizing the separation of vomiting as a side effect.

Further, Compound (I) has an amide structure containing a piperazine ring at the 2-position of the benzofuran skeleton and can be converted into a pharmaceutically acceptable acid addition salt. Taking it into consideration that the water solubility of comparative Compound Q is as very low as 1 µg/ml or less, Compound (I) which by conversion into an acid addition salt, can drastically be improved with respect to water solubility is a compound which is also physically improved. For example, Compound 1 upon conversion into monohydrochloride becomes dissolved in water at a ratio of 7.4 µg/ml.

Although Compound (I) or pharmaceutically acceptable salts thereof can also be administered as they are, it is usually desirable to provide them in the form of various pharmaceutical preparations. Such pharmaceutical preparations may be used for animals and humans.

The pharmaceutical preparations according to the present invention may contain Compound (I) or a pharmaceutically acceptable salt thereof as an active ingredient, alone or as a mixture with other therapeutically effective components. Further, such pharmaceutical preparations are produced by any means which are well-known in the technical field of pharmaceutics after mixing the active ingredient with one or more pharmaceutically acceptable carriers.

It is desired to use the administration route which is the most effective in therapy such as oral administration and parenteral administration which includes intrabuccal, intratracheal, intrarectal, subcutaneous, intramuscular and intravenous administration.

The administration form includes sprays, capsules, tablets, granules, syrups, emulsions, suppositories, injections, ointments and tapes.

Liquid preparations such as emulsions and syrups, which are suitable for oral administration, can be produced using water, sugars such as sucrose, sorbitol and fructose, glycols such as polyethylene glycol and propylene glycol, oils such as sesame oil, olive oil and soybean oil, preservatives such as p-hydroxybenzoate and flavors such as strawberry flavor and peppermint. Capsules, tablets, powder and granules can be produced using excipients such as lactose, glucose, sucrose and mannitol, disintegrators such as starch and sodium alginate, lubricants such as magnesium stearate and talc, binders such as polyvinyl alcohol, hydroxypropyl cellulose and gelatin, surfactants such as fatty acid esters, and plasticizers such as glycerin.

Preparations suitable for parenteral administration comprise a sterilized aqueous agent containing the active compound, which is preferably isotonic to the blood of a patient. For example, a solution for injection is prepared using a carrier such as a salt solution, a glucose solution or a mixture of a saline solution and a glucose solution. Preparations for intrarectal administration are prepared using a carrier such as cacao fat, hydrogenated fat and hydrogenated carboxylic acid, and provided as suppositories. Sprays are prepared using an active compound itself or with a carrier which can disperse the active compound as fine particles to facilitate absorption without stimulating oral or respiratory mucosa. Examples of such carriers are lactose and glycerin. Preparations such as aerosol and dry powder can be used depending on the properties of the active compound and carriers used.

These parenteral preparations may also contain one or more auxiliary components selected from diluents, perfumes, preservatives, excipients, disintegrators, lubricants, binders, surfactants, and plasticizers, all of which are mentioned in the above oral preparations.

The effective dose and administration schedule of Compound (I) or a pharmaceutically acceptable salt thereof may vary depending on the form of administration, the age and body weight of a patient, and the type or degree of the disease to be treated, but usually, in the case of orally administration, the effective compound is administered in a dose of 0.01 mg to 1 g/adult/day, preferably 0.05 to 50 mg/adult/day, at one time or in several parts. In the case of parenteral administration such as intravenous administration, the effective compound is administered in a dose of 0.001 to 100 mg/adult/day, preferably 0.01 to 10 mg/adult/day, at one time or in several parts. However, these doses vary depending on the various conditions described above. Hereinafter, the Preparation Examples of the present invention are described.

| Preparation Example 1: Injection (amounts of ingredients per ampoule (1.0 ml)) | |
|---|---|
| Active ingredient | 10 mg |
| Water for injection | suitable amount |

After a finely ground active ingredient is dissolved in distilled water for injection, the solution is filtered and the filtrate is sterilized in an autoclave to give an injection.

| Preparation Example 2: Tablets (amounts of ingredients per tablet) | |
|---|---|
| Active ingredient | 100 mg |
| Lactose | 60 mg |
| Potato starch | 50 mg |
| Polyvinyl alcohol | 2 mg |
| Magnesium stearate | 1 mg |
| Tar pigment | suitable amount |

A finely ground active component is mixed with powdered potato starch, lactose, magnesium stearate and polyvinyl alcohol, and then compressed to form tablets.

| Preparation Example 3: Capsules (amounts of ingredients per capsule) | |
|---|---|
| Active ingredient | 100 mg |
| Lactose | 540 mg |
| Magnesium stearate | 1 mg |

A finely ground active ingredient is mixed with powdered lactose and magnesium stearate, and the resulting mixture is charged into gelatin capsules to give capsules.

BEST MODE FOR CARRYING OUT THE INVENTION

Certain embodiments of the present invention are described in the following Examples and Reference Examples. The piperazine derivatives used in the Examples are commercial products unless otherwise noted.

EXAMPLE 1

4-(3,5-Dichloro-4-pyridyl)carbamoyl-7-methoxy-2-(4-methyl-1-piperazinyl)carbonylbenzofuran (Compound 1)

Compound K (0.75 g) obtained in Reference Example 1 was dissolved in DMF (80 ml), and 1-hydroxybenzotriazole monohydrate (1.06 g), N-ethyl-N'-3-dimethylaminopropylcarbodiimide monohydrochloride (1.51 g) and 1-methylpiperazine (1.09 ml) were added thereto, and the mixture was stirred at room temperature for 8 hours. The reaction mixture was concentrated under reduced pressure, and the residue was extracted with chloroform (200 ml). The extract was washed with a saturated aqueous sodium chloride solution and dried over sodium sulfate, and the solvent was distilled off under reduced pressure. The resulting residue was purified by silica gel column chromatography (chloroform/methanol=9/1), and the concentrated residue was recrystallized from chloroform-hexane to give Compound 1 (0.75 g, 82%) as colorless crystals.

Melting point: 224–225° C.; $^1$H-NMR(DMSO-$d_6$, δ ppm): 2.12 (s, 3H), 2.20–2.37 (m, 4H), 3.57–3.70 (m, 4H), 4.07 (s, 3H), 7.25 (d, J=8 Hz, 1H), 7.63 (s, 1H), 8.07 (d, J=8 Hz, 1H), 8.77 (s, 2H), 10.6 (s, 1H). MASS, (m/z): 462($M^+$); IR(KBr, $cm^{-1}$): 1294, 1486, 1625, 1652, 3178. Elemental analysis: $C_{21}H_{20}Cl_{12}N_4O_4 \cdot 0.2H_2O$; Found (%) C: 54.07, H: 4.39, N: 11.85; Calcd. (%) C: 54.02, H: 4.40, N: 12.00.

EXAMPLE 2

4-(3,5-Dichloro-4-pyridyl)carbamoyl-2-[4-(2-hydroxyethyl)-1-piperazinyl]carbonyl-7-methoxybenzofuran (Compound 2)

Compound 2 (0.24 g, 62%) was obtained as colorless crystals in the same procedure as in Example 1 using Compound K (0.30 g) obtained in Reference Example 1 and 1-(2-hydroxyethyl)piperazine (0.39 ml).

Melting point: 164–165° C.; $^1$H-NMR(CDCl$_3$, δ ppm): 2.58–2.62 (m, 6H), 3.66 (t, J=5 Hz, 3H), 3.83–3.87 (m, 4H), 4.09 (s, 3H), 6.94 (d, J=8 Hz, 1H), 7.75 (s, 1H), 7.81 (d, J=8 Hz, 1H), 8.58 (s, 2H). MASS (m/z): 492 ($M^+$); IR (KBr, $cm^{-1}$): 1284, 1490, 1631, 1646, 3318. Elemental analysis: $C_{22}H_{22}Cl_{12}N_4O_5 \cdot 0.2H_2O$; Found (%) C: 53.13, H: 4.49, N: 11.08; Calcd. (%) C: 53.17, H: 4.54, N: 11.27.

EXAMPLE 3

4-(3,5-Dichloro-4-pyridyl)carbamoyl-2-(4-ethyl-1-piperazinyl)carbonyl-7-methoxybenzofuran monofumarate (Compound 3)

A solution of fumaric acid in methanol was added to a compound obtained in the same procedure as in Example 1 using Compound K (1.5 g) obtained in Reference Example 1 and 1-ethylpiperazine (2.0 ml), the mixture was stirred, and the solvent was distilled off again. The resulting residue was recrystallized from ethanol to give Compound 3 (1.8 g, 94%) as colorless crystals.

Melting point: 202–204° C.; $^1$H-NMR(DMSO-$d_6$, δ ppm): 1.03 (t, J=7 Hz, 3H), 2.43 (q, J=7 Hz, 2H), 2.49–2.51 (m, 4H), 3.72 (broad s, 4H), 4.07 (s, 3H), 6.62 (s, 2H), 7.24 (d, J=8 Hz, 1H), 7.64 (s, 1H), 8.07 (d, J=8 Hz, 1H), 8.77 (s, 2H), 10.6 (s, 1H). MASS (m/z): 476 ($M^+$); IR (KBr, $cm^-$): 1288, 1627, 1646. Elemental analysis: $C_{22}H_{22}Cl_{12}N_4O_4 \cdot C_4H_4O_4$; Found (%) C: 52.66, H: 4.37, N: 9.42; Calcd. (%) C: 52.62, H: 4.42, N: 9.44.

EXAMPLE 4

4-(3,5-Dichloro-4-pyridyl)carbamoyl-2-[4-(1-hydroxy-2-propyl)-1-piperazinyl]-7-methoxycarbonylbenzofuran (Compound 4)

Compound 4 (417 mg, 63%) was obtained as colorless, crystals in the same procedure as in Example 1 using Compound K (500 mg) obtained in Reference Example 1 and Compound L (600 mg) obtained in Reference Example 2.

Melting point: 148–150° C.; $^1$H-NMR(CDCl$_3$, δ ppm): 0.92 (d, J=7 Hz, 3H), 2.49–2.52 (m, 2H), 2.73–2.77 (m, 2H), 2.82–2.96 (m, 1H), 3.09 (broad s, 1H), 3.33–3.49 (m, 2H), 3.77–3.90 (m, 3H), 4.09 (s, 3H), 6.93 (d, J=8 Hz, 1H), 7.74 (s, 1H), 7.81 (d, J=8 Hz, 1H), 7.99 (s, 1H), 8.57 (s, 2H). MASS (m/z): 506 ($M^-$); IR (KBr, $cm^{+1}$): 1276, 1488, 1592, 1608, 1681, 2910, 3155. Elemental analysis: $C_{23}H_{24}Cl_2N_4O_5$; Found (%) C: 54.28, H: 5.00, N: 10.83; Calcd. (%) C: 54.44, H: 4.78, N: 11.04.

EXAMPLE 5

4-(3,5-Dichloro-4-pyridyl)carbamoyl-2-[4-(1-hydroxy-2-butyl)-1-piperazinyl]carbonyl-7-methoxybenzofuran (Compound 5)

Compound 5 (631 mg, 66%) was obtained as colorless crystals in the same procedure as in Example 1 using Compound K (700 mg) obtained in Reference Example 1 and 1-(1-hydroxy-2-butyl)piperazine dihydrochloride (680 mg) obtained in the same procedure as in Reference Example 2.

Melting point: 192–194° C.; $^1$H-NMR(CDCl$_3$, δ ppm): 0.91 (d, J=7 Hz, 3H), 1.08–1.26 (m, 1H), 1.54–1.69 (m, 1H), 2.52–2.66 (m, 3H), 2.77–2.82 (m, 2H), 3.20 (broad s, 1H), 3.31 (t-like, J=11 Hz, 1H), 3.58 (dd, J=5 Hz, 11 Hz, 1H), 3.74–3.94 (m, 3H), 4.08 (s, 3H), 6.91 (d, J=8 Hz, 1H), 7.73 (s, 1H), 7.80 (d, J=8 Hz, 1H), 8.15 (s, 1H), 8.56 (s, 2H). MASS (m/z): 520 ($M^+$); IR (KBr, $cm^{-1}$): 1276, 1490, 1582, 1610, 1646, 1681, 2823, 2937. Elemental analysis: $C_{24}H_{26}Cl_{12}N_4O_5$; Found (%) C: 55.37, H: 5.19, N: 10.74; Calcd. (%) C: 55.28, H: 5.04, N: 10.75.

EXAMPLE 6

4-(3,5-Dichloro-4-pyridyl)carbamoyl-2-(4-hydroxypropyl-1-piperazinyl)carbonyl-7-methoxybenzofuran (Compound 6)

Compound 6 (344 mg, 60%) was obtained as colorless crystals in the same procedure as in Example 1 using Compound K (700 mg) obtained in Reference Example 1 and 1-(3-hydroxypropyl)piperazine dihydrochloride (297 mg) obtained in the same procedure as in Reference Example 2.

Melting point: 180–182° C.; $^1$H-NMR(CDCl$_3$, δ ppm): 1.74–1.80 (m, 2H), 2.59–2.68 (m, 6H), 3.77–3.84 (m, 6H), 4.09 (s, 3H), 4.51 (broad s, 1H), 6.94 (d, J=8 Hz, 1H), 7.76 (s, 1H), 7.81 (d, J=8 Hz, 1H), 7.90 (s, 1H), 8.58 (s, 2H). MASS (m/z): 506 ($M^+$); IR (KBr, $cm^{-1}$): 1286, 1623, 1652, 3156. Elemental analysis: $C_{23}H_{24}Cl_{12}N_4O_5 \cdot 0.3H_2O$; Found (%) C: 53.87, H: 4.85, N: 10.96; Calcd. (%) C: 53.87, H: 4.84, N: 10.93.

EXAMPLE 7

4-(3,5-Dichloro-4-pyridyl)carbamoyl-2-(4-hydroxybutyl-1-piperazinyl)carbonyl-7-methoxybenzofuran (Compound 7)

Compound 7 (147 mg, 22%) was obtained as colorless crystals in the same procedure as in Example 1 using Compound K (500 mg) obtained in Reference Example 1 and 1-(4-hydroxybutyl)piperazine dihydrochloride (700 mg) obtained in the same procedure as in Reference Example 2.

Melting point: 227–229° C.; $^1$H-NMR(CDCl$_3$, δ ppm): 1.69 (broad s, 4H), 2.46 (broad s, 2H), 2.58–2.61 (m, 4H), 3.61 (broad s, 2H), 3.87 (broad s, 4H), 4.09 (s, 3H), 6.94 (d, J=8 Hz, 1H), 7.76 (s, 1H), 7.81 (d, J=8 Hz, 1H), 7.90 (s, 1H), 8.57 (s, 2H). MASS (m/z): 520 (M$^+$); IR (KBr, cm$^{-1}$): 1286, 1627, 1646. Elemental analysis: $C_{24}H_{26}Cl_{12}N_4O_5$; Found (%) C: 55.02, H: 5.16, N: 10.49; Calcd. (%) C: 55.28, H: 5.04,, N: 10.75.

EXAMPLE 8

4-(3,5-Dichloro-4-pyridyl)carbamoyl-2-[4-(1,3-dihydroxy-2-propyl)-1-piperazinyl]carbonyl-7-methoxybenzofuran (Compound 8)

Compound 8 (86 mg, 63%) was obtained as colorless crystals in the same procedure as in Example 1 using Compound K (100 mg) obtained in Reference Example 1 and 1-(1,3-dihydroxy-2-propyl)piperazine dihydrochloride (85 mg) obtained in the same procedure as in Reference Example 2.

Melting point: 249–250° C.; $^1$H-NMR(DMSO-d$_6$, δ ppm): 2.49–2.55 (m, 1H), 2.72 (broad s, 4H), 3.42–3.54 (m, 4H), 3.66 (s, 4H), 4.07 (s, 3H), 4.35 (broad s, 2H), 7.24 (d, J=8 Hz, 1H), 7.61 (s, 1H), 8.06 (d, J=8 Hz, 1H), 8.77 (s, 2H), 10.61 (s, 1H). MASS (m/z): 520 (M$^+$); IR (KBr, cm$^{-1}$): 1274, 1288, 1589, 1683, 3415. Elemental analysis: $C_{24}H_{26}Cl_2N_4O_5$; Found (%) C: 55.02, H: 5.16, N: 10.49; Calcd. (%) C: 55.28, H: 5.04, N: 10.75.

EXAMPLE 9

4-(3,5-Dichloro-4-pyridyl)carbamoyl-2-{4-[2-(2-hydroxyethoxy)ethyl]-1-piperazinyl}carbonyl-7-methoxybenzofuran (Compound 9)

Compound 9 (466 mg, 47%) was obtained as colorless crystals in the same procedure as in Example 1 using Compound K (700 mg) obtained in Reference Example 1 and 1-[2-(2-hydroxyethoxy)ethyl]piperazine (1.2 ml).

Melting point: 132–133° C.; $^1$H-NMR(CDCl$_3$, δ ppm): 2.58–2.66 (m, 6H), 3.61–3.69 (m, 6H), 3.85 (broad s, 4H), 4.08 (s, 3H), 6.92 (d, J=8 Hz, 1H), 7.73 (s, 1H), 7.79 (d, J=8 Hz, 1H), 8.07 (s, 1H), 8.56 (s, 2H). MASS (m/z): 536 (M$^+$); IR (KBr, cm$^{-1}$): 1282, 1294, 1618, 1639, 3189. Elemental analysis: $C_{24}H_{26}Cl_2N_4O_6$; Found (%) C: 53.37, H: 5.02, N: 10.36; Calcd. (%) C: 53.37, H: 4.89, N: 10.43.

EXAMPLE 10

4-(3,5-Dichloro-4-pyridyl)carbamoyl-7-methoxy-2-(3,4,5-trimethyl-1-piperazinyl)carbonylbenzofuran (Compound 10)

Compound 10 (643 mg, 71%) was obtained as colorless crystals in the same procedure as in Example 1 using Compound K (700 mg) obtained in Reference Example 1 and 1,2,6-trimethylpiperazine dihydrochloride (1.75 g) obtained in the same procedure as in Reference Example 2.

Melting point: 234–236° C.; $^1$H-NMR(CDCl$_3$, δ ppm): 1.13 (broads, 1H), 2.19–2.27 (m, 2H), 2.29 (s, 3H), 2.63–2.75 (m, 2H), 3.05–3.15 (m, 2H), 4.08 (s, 3H), 4.40–4.50 (m, 2H), 6.90 (d, J=8 Hz, 1H), 7.70 (s, 1H), 7.79 (d, J=8 Hz, 1H), 8.16 (s, 1H), 8.56 (s, 2H). MASS (m/z): 490 (M$^+$); IR (KBr, cm$^{-1}$): 1174, 1278, 1405, 1583, 1612, 1672. Elemental analysis: $C_{23}H_{24}Cl_2N_4O_4$; Found (%) C: 55.85, H: 4.97, N: 11.4; Calcd. (%) C: 55.81, H: 4.97, N: 11.3.

EXAMPLE 11

4-(3,5-Dichloro-4-pyridyl)carbamoyl-2-(3,5-dimethyl-4-hydroxyethyl-7-methoxy-1-piperazinyl)carbonylbenzofuran (Compound 11)

Compound 11 (213 mg, 31%) was obtained as colorless crystals in the same procedures in Example 1 using Compound K (500 mg) obtained in Reference Example 1 and 1-hydroxyethyl-2,6-dimethylpiperazine dihydrochloride (770 mg) obtained in the same procedure as in Reference Example 2.

Melting point: 221–223° C.; $^1$H-NMR(CDCl$_3$, δ ppm): 1.13 (broad s, 6H), 1.73 (broad s, 1H), 2.32 (broad s, 1H), 2.68–2.71 (m, 2H), 2.80 (t, J=6 Hz, 2H), 3.08–3.10 (m, 1H), 3.58–3.62 (m, 2H), 4.08 (s, 3H), 4.34–4.36 (m, 1H), 6.91 (d, J=8 Hz, 1H), 7.72 (s, 1H), 7.80 (d, J=8 Hz, 1H), 8.19 (s, 1H), 8.56 (s, 2H). MASS (m/z): 520 (M$^+$); IR (KBr, cm$^{-1}$): 1295, 1488, 1592, 1618, 1637, 1654, 3156. Elemental analysis: $C_{24}H_{26}Cl_2N_4O_5$; Found (%) C: 55.34, H: 4.94, N: 10.56; Calcd. (%) C: 55.28, H: 5.04, N: 10.75.

EXAMPLE 12

4-(3,5-Dichloro-4-pyridyl)carbamoyl-7-methoxy-2-(1-piperazinyl)carbonylbenzofuran (Compound 12)

Compound 12 (2.0 g, 74%) was obtained as colorless crystals in the same procedure as in Example 1 using Compound K (2.3.g) obtained in Reference Example 1 and piperazine (7.8 g).

$^1$H-NMR(DMSO-d$_6$, δ ppm) 2.74–2.76 (m, 4H); 3.63 (broad s, 4H), 4.07 (s, 3H), 7.23 (d, J=9 Hz, 1H), 7.63 (s, 1H), 8.06 (d, J=9 Hz, 1H), 8.75 (s, 2H). MASS (m/z): 448 (M$^+$).

EXAMPLE 13

4-[2-(3,5-Dichloro-4-pyridyl)-1-oxoethyl]-2-(4-methyl-1-piperazinyl)carbonyl-7-methoxybenzofuran (Compound 13)

4-[2-(3,5-Dichloro-4-pyridyl)-1-oxoethyl]-7-methoxybenzofuran-2-carboxylic acid (Compound M, 5.8 g) obtained in Reference Example 3 was dissolved in DMF (700 ml), and 1-hydroxybenzotriazole monohydrate (8.4 g), N-ethyl-N'-3-dimethylaminopropylcarbodiimide monohydrochloride (11.6 g) and 1-methylpiperazine (6.8 ml) were added thereto, and the mixture was stirred at room temperature for 5 hours. After the solvent was distilled off under reduced pressure, the residue was extracted with chloroform, washed with a saturated aqueous sodium chloride solution, and dried over magnesium sulfate. The solvent was distilled off under reduced pressure, and the resulting residue was purified by silica gel column chromatography (chloroform:methanol 80:1 to 20:1) and then recrystallized from ethanol to give Compound 13 (5.5 g, 79%) as colorless crystals.

Melting point: 160–161° C.; $^1$H-NMR(CDCl$_3$, δ ppm): 2.33 (m, 3H), 2.45–2.49 (m, 4H), 3.81–3.85 (m, 4H), 4.12 (s, 3H), 4.74 (s, 2H), 6.96 (d, J=8.5 Hz, 1H), 7.88 (s, 1H), 8.03 (d, J=8.5 Hz, 1H), 8.54 (s, 2H). MASS (m/z): 461 (M$^+$); IR (KBr, cm$^{-1}$): 1207, 1297, 1405, 1583, 1618, 1666. Elemental analysis: $C_{22}H_{21}Cl_2N_3O_4$; Found (%) C: 57.16, H: 4.65, N: 9.03; Calcd. (%) C: 57.15, H: 4.58, N: 9.09.

EXAMPLE 14

4-[2-(3,5-Dichloro-4-pyridyl)-1-oxoethyl]-2-[4-(2-hydroxyethyl)-1-piperazinyl]carbonyl-7-methoxybenzofuran (Compound 14)

Compound 14 (2.68 g, 69%) was obtained as colorless crystals in the same procedure as in Example 13 using Compound M (3.0 g) obtained in Reference Example 3 and 1-(2-hydroxyethyl)piperazine (3.9 ml).

Melting point: 155–156° C.; $^1$H-NMR(CDCl$_3$, δ ppm): 2.58–2.62 (m, 6H), 3.66 (broad, 2H), 3.84 (broad, 4H), 4.12

(s, 3H), 4.74 (s, 2H), 6.96 (d, J=8.5 Hz, 1H), 7.89 (s, 1H), 8.03 (d, J=8.5 Hz, 1H), 8.54 (s, 2H). MASS (m/z): 491 (M$^+$); IR (KBr, cmu$^{-1}$): 1211, 1284, 1305, 1402, 1577, 1629, 1662. Elemental analysis: $C_{23}H_{23}Cl_2N_3O_5 \cdot 0.4H_2O$; Found (%) C: 55.37, H: 4.76, N: 8.27; Calcd. (%) C: 55.30, H: 4.80, N: 8.41.

EXAMPLE 15

4-[2-(3,5-Dichloro-4-pyridyl)-1-oxoethyl]-2-(4-ethyl-1-piperazinyl)-7-methoxycarbonylbenzofuran Monofumarate (Compound 15)

A solution of fumaric acid in methanol was added to a compound obtained in the same procedure as in Example 13 using Compound M (1.5 g) obtained in Reference Example 3 and 1-ethylpiperazine (2.0 ml), the mixture was stirred, and the solvent was distilled off again. The resulting residue was recrystallized from ethanol to give Compound 15 (1.5 g, 65%) as colorless crystals.

Melting point: 196–198° C.; $^1$H-NMR(CDCl$_3$, δ ppm): 1.02 (t, J=7 Hz, 3H), 2.42 (q, J=7 Hz, 2H), 2.47–2.51 (m, 4H), 3.70 (m, 4H), '4.11 (s, 3H), 4.87 (s, 2H), 6.62 (s, 2H), 7.25 (d, J=8 Hz, 1H1), 7.70 (s, 1H), 8.37 (d, J=8 Hz, 1H), 8.68 (s, 2H). MASS (m/z): 475 (M$^+$); IR (KBr, cm–$^1$l): 1209, 1402, 1579, 1635. Elemental analysis: $C_{23}H_{23}Cl_2N_3O_4 \cdot C_4H_4O_4 \cdot 0.6H_2O$; Found (%) C: 53.80, H: 4.71, N: 6.88; Calcd. (%) C: 53.76, H: 4.71, N: 6.97.

EXAMPLE 16

4-[2-(3,5-Dichloro-4-pyridyl)-1-oxoethyl]-2-(4-isopropyl-1-piperazinyl)carbonyl-7-methoxybenzofuran Monofumarate (Compound 16)

4-[2-(3,5-Dichloro-4-pyridyl)-1-oxoethyl]-7-methoxy-2-(1-piperazinylcarbonyl)benzofuran (Compound O, 0.80 g) obtained in Reference Example 5 was dissolved in anhydrous DMF (40 ml), and 2-bromopropane (1.67 ml), triethylamine (2.48 ml) and potassium iodide (0.80 mg) were added thereto, and the mixture was stirred at 100° C. for 2 hours. The solvent was distilled off under reduced pressure, the residue was extracted with chloroform, washed with a saturated aqueous sodium chloride solution and dried over sodium sulfate, and the solvent was distilled off. The residue was purified by silica gel column chromatography (3% triethylamine-ethyl acetate), and the residue was dissolved in chloroform. A solution of fumaric acid in methanol was added thereto, the mixture was stirred, and the solvent was distilled off again. The resulting solid was recrystallized from ethanol to give Compound 16 (0.50 g, 37%) as colorless crystals.

Melting point: 195–196° C.; $^1$H-NMR(DMSO-d$_6$, δ ppm): 0.97 (d, J=6.5 Hz, 6H), 2.49–2.50 (m, 4H), 2.67–2.75 (m, 1H), 3.60–3.70 (m, 4H), 4.09 (s, 3H), 4.85 (s, 2H), 6.60 (s, 2H), 7.23 (d, J=8.5 Hz, 1H), 7.68 (s, 1H), 8.35 (d, J=8.5 Hz, 1H), 8.67 (s, 2H). MASS (m/z): 489 (M$^+$); IR (KBr, cm$^{-1}$): 1180, 1294, 1305, 1405, 1579, 1633, 1656. Elemental analysis: $C_{24}H_{25}Cl_2N_3O_4 \cdot C_4H_4O_4 \cdot 0.4H_2O$; Found (%) C: 54.79, H: 4.92, N: 6.81; Calcd. (%) C: 54.80, H: 4.89, N: 6.84.

EXAMPLE 17

4-[2-(3,5-Dichloro-4-pyridyl)-1-oxoethyl]-2-(4-ethoxyethyl-1-piperazinyl)carbonyl-7-methoxybenzofuran Monofumarate (Compound 17)

Compound 17 (0.34 g, 34%) was obtained as colorless crystals in the same procedure as in Example 16 using Compound O (0.70 g) obtained in Reference Example 5 and 1-(2-ethoxyethyl)piperazine.

Melting point: 184–185° C.; $^1$H-NMR(DMSO-d$_6$, δ ppm): 1.07 (t, J=7 Hz, 3H), 3.35–3.65 (m, 12H), 4.08 (s, 3H), 4.84 (s, 2H), 6.60 (s, 2H), 7.23 (d, J=8.5 Hz, 1H), 7.67 (s, 1H), 8.34 (d, J=8.5 Hz, 1H), 8.66 (s, 2H). MASS (m/z): 519 (M$^+$); IR (KBr, cm$^{-1}$): 1176, 1267, 1403, 1581, 1629, 1668. Elemental analysis: $C_{25}H_{27}Cl_2N_3O_5 \cdot C_4H_4O_4$; Found (%) C: 54.98, H: 4.89, N: 6.62; Calcd. (%) C: 54.73, H: 4.91, N: 6.60.

EXAMPLE 18

4-[2-(3,5-Dichloro-4-pyridyl)-1-oxoethyl]-2-[4-(1-hydroxy-2-propyl)-1-piperazinyl]carbonyl-7-methoxybenzofuran (Compound 18)

Compound 18 (0.52 g, 56%) was obtained as colorless crystals in the same procedure as in Example 13 using Compound M (0.70 g) obtained in Reference Example 3 and 1-(1-hydroxy-2-propyl)piperazine dihydrochloride (Compound L, 0.84 g) obtained in Reference Example 2.

Melting point: 187–189° C.; $^1$H-NMR(CDCl$_3$, δ ppm): 0.92 (d, J=7 Hz, 3H), 2.45–2.52 (m, 2H), 2.68–2.78 (m, 2H), 2.83–2.92 (m, 1H), 3.33–3.48 (m, 1H), 3.71–3.87 (m, 4H), 4.12 (s, 3H), 4.74 (s, 2H), 6.96 (d, J=8 Hz, 1H), 7.89 (s, 1H), 8.02 (d, J=8 Hz, 1H), 8.54 (s, 2H). MASS (m/z): 505 (M$^+$); IR (KBr, cm$^{-1}$): 1207, 1403, 1560, 1618, 1635. Elemental analysis: $C_{24}H_2Cl_2N_3O_5$; Found (%) C: 56.82, H: 4.84, N: 8.30; Calcd. (%) C: 56.92, H: 4.99, N: 8.30.

EXAMPLE 19

4-[2-(3,5-Dichloro-4-pyridyl)-1-oxoethyl]-2-[4-(1-hydroxy-2-butyl)-1-piperazinyl]carbonyl-7-methoxybenzofuran (Compound 19)

Compound 19 (0.31 g, 32%) was obtained as colorless crystals in the same procedure as in Example 13 using Compound M (0.70 g) obtained in Reference Example 3 and 1-(1-hydroxy-2-butyl)piperazine dihydrochloride (0.90 g) obtained in the same procedure as in Reference Example 2.

Melting point: 150–152° C.; $^1$H-NMR(CDCl$_3$, δ ppm): 0.91 (t, J=8 Hz, 3H), 1.10–1.27 (m, 1H), 1.57–1.68 (m, 1H), 2.54–2.66 (m, 3H), 2.78–2.83 (m, 2H), 3.17–3.19 (m, 1H), 3.31 (t-like, J=11 Hz, 1H), 3.59–3.61 (m, 1H), 3.70–3.85 (m, 3H), 4.12 (s, 3H), 4.73 (s, 2H), 6.97 (d, J=8 Hz, 1H), 7.88 (s, 1H), 8.03 (d, J=8 Hz, 1H), 8.54 (s, 2H). MASS (m/z): 520 (M$^+$); IR (KBr, cm$^{-1}$): 1207, 1403, 1567, 1583, 1625, 1673. Elemental analysis: $C_{25}H_{27}Cl_2N_3O_5$; Found (%) C: 57.66, H: 5.19, N: 7.84; Calcd. (%) C: 57.69, H: 5.24, N: 8.08.

EXAMPLE 20

4-[2-(3,5-Dichloro-4-pyridyl)-1-oxoethyl]-2-[4-(3-hydroxypropyl)-1-piperazinyl]carbonyl-7-methoxybenzofuran (Compound 20)

Compound 20 (0.35 g, 38%) was obtained as colorless crystals in the same procedure as in Example 13 using Compound M (0.70 g) obtained in Reference Example 3 and 1-(3-hydroxypropyl)piperazine dihydrochloride (0.84 g) obtained in the same procedure as in Reference Example 2.

Melting point: 162–163° C.; $^1$H-NMR(CDCl$_3$, δ ppm): 1.76 (quintet, J=6 Hz, 2H), 2.58–2.67 (m, 6H), 3.80–3.84 (m, 6H), 4.12 (s, 3H), 4.73 (s, 2H), 6.96 (d, J=9 Hz, 1H), 7.89 (s, 1H), 8.02 (d, J=9 Hz, 1H), 8.54 (s, 2H). MASS (m/z): 505 (M$^+$); IR (KBr, cm$^{-1}$): 1294, 1405, 1618, 1629.

Elemental analysis: $C_{24}H_{25}Cl_2N_3O_5$; Found (%) C: 56.88, H: 4.93, N: 8.12; Calcd. (%) C: 56.92, H: 4.99, N: 8.30.

EXAMPLE 21

4-[2-(3,5-Dichloro-4-pyridyl)-1-oxoethyl]-2-[4-(4-hydroxybutyl)-1-piperazinyl]carbonyl-7-methoxybenzofuran (Compound 21)

Compound 21 (0.25 g, 26%) was obtained as colorless crystals in the same procedure as in Example 13 using Compound M (0.70 g) obtained in Reference Example 3 and 1-(4-hydroxybutyl)piperazine dihydrochloride (2.11 g) obtained in the same procedure as in Reference Example 2.

Melting point: 120–121° C.; $^1$H-NMR(CDCl$_3$, δ ppm): 1.69 (broad s, 4H), 2.40–2.45 (m, 2H), 2.57–2.60 (m, 4H), 3.60–3.63 (m, 2H), 3.85–3.90 (m, 4H), 4.12 (s, 3H), 4.73 (s, 2H), 6.96 (d, J=8 Hz, 1H), 7.89 (s, 1H), 8.03 (d, J=8 Hz, 1H), 8.54 (m, 2H). MASS (m/z): 519 (M$^+$); IR (KBr, cm$^{-1}$): 1265, 1311, 1407, 1581, 1618, 2919, 2931. Elemental analysis: $C_{25}H_{27}Cl_2N_3O_5$; Found (%) C: 57.55, H: 5.24, N: 8.08; Calcd. (%) C: 57.69, H: 5.24, N: 8.00.

EXAMPLE 22

4-[2-(3,5-Dichloro-4-pyridyl)-1-oxoethyl]-2-[4-(1,3-dihydroxy-2-propyl)-1-piperazinyl]carbonyl-7-methoxybenzofuran (Compound 22)

Compound 22 (0.45 g, 33%) was obtained as colorless crystals in the same procedure as in Example 13 using Compound M (1.0 g) obtained in Reference Example 3 and 1-(1,3-dihydroxy-2-propyl)piperazine dihydrochloride (3.23 g) obtained in the same procedure as in Reference Example 2.

Melting point: 213–215° C.; $^1$H-NMR(CDCl$_3$, δ ppm): 2.81–2.83 (m, 4H), 3.67 (d, J=6 Hz, 4H), 3.80–3.83 (m, 4H), 4.11 (s, 3H), 4.73 (s, 2H), 6.96 (d, J=8 Hz, 1H), 7.88 (s, 1H), 8.03 (d, J=8 Hz, 1H), 8.54 (s, 2H). MASS (m/z): 521 (M$^+$); IR (KBr, cm$^{-1}$): 1207, 1290, 1403, 1446, 1583, 1610, 1683, 2983, 3328. Elemental analysis: $C_{24}H_{25}Cl_2N_3O_6$; Found (%) C: 55.30, H: 4.97, N: 7.80; Calcd. (%) C: 55.17, H: 4.83, N: 8.05.

EXAMPLE 23

4-[2-(3,5-Dichloro-4-pyridyl)-1-oxoethyl]-2-{4-[2-(2-hydroxyethoxy)ethyl]-1-piperazinyl}carbonyl-7-methoxybenzofuran (Compound 23)

Compound 23 (0.70 g, 50%) was obtained as colorless crystals in the same procedure as in Example 13 using Compound M (1.0 g) obtained in Reference Example 3 and 1-[2-(2-hydroxyethoxy)ethyl]piperazine (3.46 ml).

Melting point: 132–133° C.; $^1$H-NMR(CDCl$_3$, δ ppm): 2.58–2.65 (m, 6H), 3.60–3.69 (m, 6H), 3.85–3.87 (m, 4H), 4.12 (s, 3H), 4.73 (s, 2H), 6.96 (d, J=9 Hz, 1H), 7.88 (s, 1H), 8.03 (d, J=9 Hz, 1H), 8.53 (s, 2H). MASS (m/z): 535 (M$^+$); IR (KBr, cm$^{-1}$): 1118, 1203, 1305, 1405, 1560, 1629, 1635, 1672. Elemental analysis: $C_{25}H_{27}Cl_2N_3O_6$; Found (%) C: 56.19, H: 5.12, N: 7.58; Calcd. (%) C: 55.97, H: 5.08, N: 7.83.

EXAMPLE 24

4-[2-(3,5-Dichloro-4-pyridyl)-1-oxoethyl]-2-(1-piperazinyl)carbonyl-7-methoxybenzofuran Monohydrochloride (Compound 24)

A solution of hydrochloric acid in ethyl acetate was added to a compound obtained in the same procedure as in Example 13 using Compound M (1.0 g) obtained in Reference Example 3 and piperazine (4.53 g), the mixture was stirred, and the solvent was distilled off again. The resulting residue was recrystallized from ethanol to give Compound 24 (0.62 g, 49%) as colorless crystals.

$^1$H-NMR(DMSO-d$_6$, δ ppm): 3.16–3.46 (m, 6H), 3.89 (broad s, 2H), 4.09 (s, 3H), 4.85 (s, 2H), 7.25 (d, J=9 Hz, 1H), 7.78 (s, 1H), 8.36 (d, J=9 Hz, 1H), 8.66 (s, 2H). MASS (m/z): 447 (M$^+$).

EXAMPLE 25

4-[2-(3,5-Dichloro-4-pyridyl)-1-oxoethyl]-7-methoxy-2-(3,4,5-trimethyl-1-piperazinyl)carbonylbenzofuran (Compound 25)

Compound 13 (0.23 g, 20%) was obtained as colorless crystals in the same procedure as in Example 25 using Compound M (0.91 g) obtained in Reference Example 3 and 1,2,6-trimethylpiperazine di(trifluoroacetate) (2.88 g) obtained in the same procedure as in Reference Example 16.

Melting point: 173–174° C.; $^1$H-NMR(CDCl$_3$, δ ppm): 1.13 (broad s, 6H), 2.21–2.30 (m, 4H), 2.28 (s, 3H), 2.65–2.75 (broad s, 1H), 3.05–3.15 (broad s, 1H), 4.11 (s, 3H), 4.73 (s, 2H), 6.96 (d, J=9 Hz, 1H), 7.87 (s, 1H), 8.04 (d, J=9 Hz, 1H), 8.53 (s, 2H). MASS (m/z): 489 (M$^+$); IR (KBr, cm$^{-1}$): 1265, 1278, 1309, 1583, 1612, 1672. Elemental analysis: $C_{24}H_{25}Cl_2N_3O_4$; Found (%) C: 58.85, H: 5.12, N: 8.45; Calcd. (%) C: 58.77, H: 5.15, N: 8.57.

EXAMPLE 26

4-[2-(3,5-Dichloro-4-pyridyl)-1-oxoethyl]-2-(3,5-dimethyl-4-hydroxyethyl-1-piperazinyl)carbonyl-7-methoxybenzofuran (Compound 26)

Compound 26 (0.30 g, 43%) was obtained as colorless crystals in the same procedure as in Example 13 using Compound M(0.50 g) obtained in Reference Example 3 and 1,6-dimethyl-2-hydroxyethylpiperazine dihydrochloride (0.77 g) obtained in the same procedure as in Reference Example 2.

Melting point: 187–188° C.; $^1$H-NMR(CDCl$_3$, δ ppm): 1.14 (broad s, 1H), 1.65 (broad s, 1H), 2.23–2.26 (m, 1H), 2.69–2.72 (m, 2H), 2.80 (t, J=6 Hz, 2H), 3.10–3.11 (m, 1H), 3.57–3.63 (m, 2H), 4.12 (s, 3H), 4.32–4.36 (m, 1H), 4.74 (s, 2H), 6.97 (d, J=8 Hz, 1H), 7.88 (s, 1H), 8.03 (d, J=8 Hz, 1H), 8.54 (s, 2H). MASS (m/z): 519 (M$^+$); IR (KBr, cm$^{-1}$): 1211, 1286, 1309, 1407,1583, 1621, 1670. Elemental analysis: $C_{25}H_{27}Cl_2N_3O_5$; Found (%) C: 57.94, H: 5.23, N: 8.04; Calcd. (%) C: 57.69, H: 5.24, N: 8.08.

EXAMPLE 27

4-[2-(3,5-Dichloro-4-pyridyl)ethyl]-7-methoxy-2-(4-methyl-1-piperazinyl)carbonylbenzofuran Monofumarate (Compound 27)

A solution of fumaric acid in methanol was added to a compound obtained in the same procedure as in Example 13 using 4-[2-(3,5-dichloro-4-pyridyl)ethyl]-7-methoxybenzofuran-2-carboxylic acid (Compound N, 1.0 g) obtained in Reference Example 4 and 1-methylpiperazine (1.5 ml), the mixture was stirred, and the solvent was distilled off again. The resulting residue was recrystallized from ethanol to give Compound 27 (1.38 g, 90%) as colorless crystals.

Melting point: 186–187° C.; $^1$H-NMR(DMSO-d$_6$, δ ppm): 2.24 (s, 1H), 2.42–2.49 (m, 4H), 3.04–3.08 (m, 2H), 3.15–3.19 (m, 2H), 3.64–3.70 (m, 4H), 3.91 (s, 3H), 6.61 (s, 2H), 6.94 (d, J=8 Hz, 1H), 6.99 (d, J=8 Hz, 1H), 7.32 (s, 1H), 8.57 (s, 2H). MASS (m/z): 447 (M$^+$); IR (KBr, cm$^-$): 977, 1172, 1272, 1295, 1438, 1560, 1575, 1640. Elemental analysis: $C_{22}H_{23}Cl_2N_3O_3 \cdot C_4H_4O_4 \cdot 0.3H_2O$; Found (%) C: 54.86, H: 4.85, N: 7.23; Calcd. (%) C: 54.80, H: 4.88, N: 7.37.

EXAMPLE 28

4-[2-(3,5-Dichloro-4-pyridyl)ethyl]-2-[4-(2-hydroxyethyl)-1-piperazinyl]carbonyl-7-methoxybenzofuran Fumarate (Compound 28)

A solution of fumaric acid in methanol was added to a compound obtained in the same procedure as in Example 13 using Compound N (0.72 g) obtained in Reference Example 4 and 1-(2-hydroxyethyl)piperazine (1.2 ml), the mixture was stirred, and the solvent was distilled off again. The resulting residue was recrystallized from ethanol to give Compound 28 (0.89 g, 84%) as colorless crystals.

Melting point: 184–185° C.; $^1$H-NMR(DMSO-d$_6$, δ ppm): 2.42–2.49 (m, 2H), 3.03–3.07 (m, 2H), 3.14–3.18 (m, 2H) 3.40–3.67 (m, 10H), 3.91 (s, 3H), 6.60 (s, 2H), 6.94 (d, J=8 Hz, 1H), 6.99 (d, J=8 Hz, 1H), 7.31 (s, 1H), 8.56 (s, 2H). MASS (m/z): 525 (M$^+$); IR (KBr, cm$^{-1}$): 1091, 1292, 1508, 1652. Elemental analysis: $C_{23}H_{25}Cl_2N_3O_4 \cdot 0.5C_4H_4O_4$; Found (%) C: 56.09, H: 5.14, N: 7.78; Calcd. (%) C: 55.98, H: 5.07, N: 7.83.

EXAMPLE 29

4-(3,5-Dichloro-4-pyridyl)carbamoyl-2-[3,5-dimethyl-4-(3-hydroxypropyl)-1-piperazinyl]carbonyl-7-ethoxybenzofuran (Compound 29)

Compound 29 (790 mg, 28%) was obtained as colorless crystals in the same procedure as in Example 1 using Compound K (2.0 g) obtained in Reference Example 1 and 2,6-dimethyl-1-hydroxypropylpiperazine dihydrochloride (3.7 g) obtained in the same procedure as in Reference Example 2.

$^1$H-NMR(CDCl$_3$, δ ppm): 1.21 (broad s, 6H), 1.59 (broad s, 1H), 1.62–1.70 (m, 2H), 2.58–2.62 (m, 2H), 2.80–2.90 (m, 2H), 3.03–3.10 (m, 1H), 3.40–3.42 (m, 1H), 3.74–3.78 (m, 2H), 4.11 (s, 3H), 4.34–4.36 (m, 1H), 6.96 (d, J=8 Hz, 1H), 7.76 (s, 1H), 7.78 (s, 1H), 7.82 (d, J=8 Hz, 1H), 8.59 (s, 2H). Elemental analysis: $C_{25}H_{28}C_{12}N_4O_5$; Found (%) C: 56.27, H: 5.32, N: 10.42; Calcd. (%) C: 56.08, H: 5.27, N: 10.46.

EXAMPLE 30

4-[2-(3,5-Dichloro-4-pyridyl)-1-oxoethyl]-2-(3,5-dimethyl-4-hydroxypropyl-1-piperazinyl)carbonyl-7-methoxybenzofuran Monofumarate (Compound 30)

A solution of fumaric acid in methanol was added to a compound obtained in the same procedure as in Example 13 using Compound M (2.0 g) obtained in Reference Example 3 and 2,6-dimethyl-1-hydroxypropylpiperazine dihydrochloride (3.7 g) obtained in the same procedure as in Reference Example 2, the mixture was stirred, and the solvent was distilled off again. The resulting residue was recrystallized from ethanol to give Compound 30 (700 mg, 20%) as colorless crystals.

$^1$H-NMR(DMSO-d$_6$, δ ppm): 1.02 (broad s, 1H), 1.45–1.49 (m, 2H), 2.50–2.58 (m, 2H), 2.72–2.76 (m, 2H), 3.20–3.40 (m, 6H), 4.11 (s, 3H), 4.87 (s, 2H), 6.61 (s, 2H), 7.23 (d, J=8 Hz, 1H), 7.69 (s, 1H), 8.34 (d, J=8 Hz, 1H), 8.68 (s, 2H). MASS (m/z): 533 (M$^+$); Elemental analysis: $C_{26}H_{29}Cl_2N_3O_5 \cdot C_4H_4O_4 \cdot 0.5H_2O$; Found (%) C: 54.69, H: 5.17, N: 6.10; Calcd. (%) C: 54.64, H: 5.20, N: 6.37.

REFERENCE EXAMPLE 1

4-[(3,5-Dichloro-4-pyridyl)carbamoyl]-7-methoxybenzofuran-2-carboxylic Acid (Compound K)

(Step 1): Ethyl 4-Formyl-7-methoxybenzofuran-2-carboxylate

Ethyl 7-methoxybenzofuran-2-carboxylate (10 g) was dissolved in anhydrous methylene chloride (200 ml), dichloromethyl methyl ether (8.2 ml) and titanium tetrachloride (10 ml) were dropwise added thereto under cooling on ice, and the mixture was stirred as such for 30 minutes. The mixture was returned to room temperature and stirred for 1.5 hours, and 1 mol/L aqueous HCl was dropwise added thereto, to decompose the remaining titanium tetrachlorides, followed by extraction with chloroform. The extract was washed with 1 N aqueous NaOH and then with a saturated aqueous sodium chloride solution and dried over sodium sulfate, and the solvent was distilled off. The residue was suspended in ether and the precipitated crystals were collected by filtration to give the desired compound (8.9 g, 79%) as colorless crystals.

$^1$H-NMR(CDCl$_3$, δ ppm): 1.43 (t, J=7 Hz, 13H), 4.12 (s, 3H), 4.46 (q, J=7 Hz, 2H), 7.01 (d, J=8 Hz, 1H), 7.75 (d, J=8 Hz, 1H), 8.22 (s, 1H), 10.0 (s, 1H). MASS (m/z): 248 (M$^+$).

(Step 2): 2-Ethoxycarbonyl-7-methoxybenzofuran-4-carboxylic Acid

Ethyl 4-formyl-7-methoxybenzofuran-2-carboxylate (9.5 g) obtained in step 1 was dissolved in acetic acid (800 ml) /water 200 ml), sulfamic acid (19 g) and sodium chlorite (14 g) were added thereto, and the mixture was stirred at room temperature for 7 hours. Crystals precipitated by adding water (1 L) were collected by filtration and washed with water to give the desired compound (9.4 g, 93%) as colorless crystals.

$^1$H-NMR(DMSO-d$_6$, δ ppm): 1.36 (t, J=7 Hz, 3H), 4.05 (s, 3H), 4.38 (q, J=7 Hz, 2H), 7.23 (d, J=9 Hz, 1H), 7.93 (s, 1H), 7.95 (d, J=9 Hz, 1H). MASS (m/z): 264 (M$^+$).

(Step 3): Ethyl 4-[(3,5-Dichloro-4-pyridyl)carbamoyl]-7-methoxybenzofuran-2-carboxylate 2-Ethoxycarbonyl-7-methoxybenzofuran-4-carboxylic acid (4.5 g) was suspended in anhydrous methylene chloride (70 ml), thionyl chloride (60 ml) was added thereto, and the mixture was refluxed for 3 hours. The acid chloride obtained by concentration under reduced pressure was dried and used as such in the subsequent reaction.

4-Amino-2,6-dichloropyridine (5.5 g) was dissolved in anhydrous THF (200 ml), and sodium hydride (60% oil suspension, 1.7 g) was added thereto under cooling on ice, and the mixture was stirred for 50 minutes. After the mixture was cooled to −78° C., a solution of the previously prepared acid chloride in anhydrous methylene chloride (200 ml) was dropwise added thereto over 30 minutes. After the mixture was stirred at −78° C. for 2 hours, the reaction was quenched by dropping 1 N aqueous HCl under cooling on ice, and the reaction mixture was extracted with chloroform (800 ml). The extract was washed with 1 N aqueous HCl and then with a saturated aqueous sodium chloride solution and dried over sodium sulfate, and the solvent was distilled off under reduced pressure. The residue was suspended in ether and the precipitated crystals were collected by filtration to give the desired compound (6.1 g, 88%) as colorless crystals.

$^1$H-NMR(CDCl$_3$, δ ppm): 1.41 (t, J=7 Hz, 3H), 4.12 (s, 3H), 4.44 (q, J=7 Hz, 2H), 7.00 (d, J=8 Hz, 1H), 7.82 (d, J=8 Hz, 1H), 8.09 (s, 1H), 8.59 (s, 2H). MASS (m/z): 409(M$^+$).

(Step 4) Synthesis of Compound K

Ethyl 4-[(3,5-dichloro-4-pyridyl)carbamoyl]-7-methoxybenzofuran-2-carboxylate (6.1 g) was dissolved in methanol (80 ml), 1 N aqueous NaOH (40 ml) was added thereto under cooling on ice, and the mixture was returned to room temperature and stirred for 2 hours. The reaction mixture was acidified by dropwise adding 1 N aqueous HCl under cooling on ice, and the precipitated crystals were collected by filtration and washed with water to give Compound K (5.6 g, 98%).

$^1$H-NMR(DMSO-d$_6$, δ ppm): 4.07 (s, 3H), 7.29 (d, J=8.5 Hz, 1H), 7.90 (s, 1H), 8.08 (d, J=8.5 Hz, 1H), 8.77 (s, 2H), 10.6 (s, 1H), 13.8 (broad s, 1H). MASS (m/z): 380(M$^+$).

REFERENCE EXAMPLE 2

1-(1-Hydroxy-2-propyl)piperazine Dihydrochloride (Compound L)

(Step 1) Methyl 2-(4-Triphenylmethylpiperazinyl)propionate

1-Triphenylmethylpiperazine (1.5 g) obtained in a known method (EP330263A) was dissolved in DMF (50 ml), methyl 2-bromopropionate (2.55 ml) and triethylamine (3.2 ml) were added thereto, and the mixture was stirred at room temperature for 12 hours. The solvent was distilled off under reduced pressure, the residue was extracted with ethyl acetate, and the extract was washed with a saturated aqueous sodium chloride solution. The extract was dried over sodium sulfate and the solvent was distilled off under reduced pressure to give the desired compound (1.9 g, 98%) as colorless crystals.

$^1$H-NM(CDCl$_3$, δ ppm): 1.27 (d, J=7 Hz, 3H), 2.76 (broad s, 8H), 3.27 (q, J=7 Hz, 1H), 3.73 (s, 3H), 7.12–7.45 (m, 15H).

(Step 2) 1-(1-Hydroxy-2-propyl)-2-triphenylmethylpiperazine

Lithium aluminum hydride (350 mg) was suspended in anhydrous THF (30 ml), and a solution in anhydrous THF (35 ml) of methyl 2-(4-triphenylmethylpiperazinyl)propionate (1.9 g) obtained in step 1 was dropwise added thereto at 0° C. The mixture was stirred as such for 15 minutes, and the reaction was quenched by adding ethyl acetate. Then, anhydrous sodium sulfate and water were added thereto, and the mixture was stirred and filtered through Celite. The filtrate was distilled off under reduced pressure, the residue was extracted with ethyl acetate, and the extract was washed with a saturated aqueous sodium chloride solution. The extract was dried over sodium sulfate, and the solvent was distilled off under reduced pressure to give the desired compound (1.7 g, 97%) as colorless syrup.

$^1$H-NMR(CDCl$_3$, δ ppm): 1.13 (d, J=6 Hz, 3H), 2.54–2.57 (m, 4H), 2.74–2.78 (m, 4H), 3.24 (t-like, J=10 Hz, 1H), 3.35 (dd, J=10 Hz, 5 Hz, 1H), 3.64 (quintet, J=6 Hz, 1H), 7.12–7.28 (m, 9H), 7.46–7.48 (m, 6H).

(Step 3) Synthesis of Compound L 1-(1-Hydroxy-2-propyl)-2-triphenylmethylpiperazine (1.69 g) obtained in step 2 was dissolved in ethanol (20 ml), and a 4 mol/l hydrogen chloride solution in ethyl acetate (10 ml) was dropwise added thereto. The mixture was stirred at room temperature for 10 minutes. The solvent was distilled off under reduced pressure, the residue was suspended in ethyl ether, and the precipitated crystals were collected by filtration to give Compound L (840 mg, 89%).

$^1$H-NMR(DMSO-d$_6$, δ ppm): 1.27 (d, J=7 Hz, 3H), 3.60–3.80 (m, 11H), 9.85 (broad s, 1H), 11.3 (broad s, 1H).

REFERENCE EXAMPLE 3

4-[2-(3,5-Dichloro-4-pyridyl)-1-oxoethyl]-7-methoxybenzofuran-2-carboxylic Acid (Compound M)

(Step 1): Ethyl 4-[2-(3,5-dichloro-4-pyridyl)-1-hydroxyethyl]-7-methoxybenzofuran-2-carboxylate N,N-Diisopropylamine (65.6 ml) was dissolved in anhydrous THF (150 ml), n-butyl lithium (a 1.54 mol/l solution in hexane, 300 ml) was dropwise added thereto at −78° C. in an argon atmosphere, and the mixture was stirred for 5 minutes. After a solution of 3,5-dichloropyridine (63 g) in anhydrous THF (600 ml) was dropwise added thereto and the mixture was stirred for 1 hour, methyl iodide (29.2 ml) was dropwise added thereto, and the mixture was stirred for 1.5 hours. Water was added thereto, the reaction mixture was extracted with ethyl acetate, the extract was washed with a saturated aqueous sodium chloride solution and dried over magnesium sulfate, and the solvent was distilled off under reduced pressure. The residue was purified by silica gel column chromatography (hexane:ethyl acetate=10:1), the resulting residue was suspended in hexane, and the precipitated crystals were collected by filtration to give 3,5-dichloropicoline (62.8 g, 91%) as colorless crystals.

N,N-Diisopropylamine (8.5 ml) was dissolved in anhydrous THF (150 ml), n-butyl lithium (a 1.65 mol/l solution in hexane, 32 ml) was dropwise added thereto at −78° C. in an argon atmosphere, and the mixture was stirred for 5 minutes. The mixture was stirred at room temperature for 3 minutes and then cooled again to −78° C., 3,5-dichloropicoline (7.2 g) was added thereto, and the mixture was stirred for 30 minutes, which was dropwise added at −78° C. over 1 hour in an argon atmosphere to a solution in anhydrous THF (500 ml) of ethyl 4-formyl-7-methoxybenzofuran-2-carboxylate (10 g) obtained in step 1 of Reference Example 1. The mixture was stirred at −78° C. for 2.5 hours and returned to room temperature, and the reaction was quenched by adding water. The reaction mixture was diluted with ethyl acetate, which was washed with a saturated aqueous sodium chloride solution and dried over sodium sulfate. The solvent was distilled off under reduced pressure. The resulting residue was suspended in isopropanol and the precipitated crystals were collected by filtration to give the desired compound (14.3 g, 87%) as colorless crystals.

$^1$H-NMR(CDCl$_3$, δ ppm): 1.43 (t, J=7 Hz, 3H), 3.32 (dd, J=13 Hz, 5 Hz, 1H), 3.60 (dd, J=13 Hz, 8.5 Hz, 1H), 4.01 (s, 3H), 4.45 (q, J=7 Hz, 2H), 5.34 (m, 1H), 6.83 (d, J=8 Hz, 1H), 7.11 (d, J=8 Hz, 1H), 7.80 (s, 1H), 8.41 (s, 2H). MASS (m/z): 409 (M$^+$).

(Step 2): Ethyl 4-[2-(3,5-Dichloro-4-pyridyl)-1-oxoethyl]-7-methoxybenzofuran-2-carboxylate Ethyl 4-[2-(3,5-dichloro-4-pyridyl)-1-hydroxyethyl]-7-methoxybenzofuran-2-carboxylate (10 g) was dissolved in acetone (200 ml), a Jones reagent (a 2.76 mmol/L solution, 9.7 ml) was dropwise added thereto under cooling on ice, and the mixture was stirred for 20 minutes. Isopropanol was added thereto, and the mixture was stirred at room temperature for 30 minutes. The solvent was distilled off under reduced pressure and the residue was extracted with chloroform. The extract was washed with a saturated aqueous sodium chloride solution and dried over magnesium sulfate, and the solvent was distilled off under reduced pressure. The residue was suspended in isopropanol and the precipitated crystals were collected by filtration to give the desired compound (8.34 g, 84%) as colorless crystals.

$^1$H-NMR(CDCl$_3$, δ ppm): 1.39 (t, J=7 Hz, 3H), 4.13 (s, 3H), 4.42 (q, J=7 Hz, 2H), 4.73 (s, 2H), 6.99 (d, J=8Hz, 1H), 8.04 (d, J=8 Hz, 1H), 8.21 (s, 1H), 8.54 (s, 2H). MASS (m/z): 407(M$^+$).

(Step 3): Compound M

Ethyl 4-[2-(3,5-dichloro-4-pyridyl)-1-oxoethyl]-7-methoxybenzofuran-2-carboxylate (6.0 g) was dissolved in methanol (60 ml), 5 N aqueous NaOH (15 ml) was added thereto under cooling on ice, and the mixture was returned to room temperature and stirred for 1 hour. Under cooling on ice, the reaction mixture was acidified by dropwise adding 1 N aqueous HCl, and the precipitated crystals were collected by filtration and washed with water to give the desired compound (5.4 g, 96%) as colorless crystals.

$^1$H-NMR(DMSO-d$_6$, δ ppm): 4.09 (s, 3H), 4.86 (s, 2H), 7.29 (d, J=8.5 Hz, 1H), 8.38 (d, J=8.5 Hz, 1H), 8.68 (s, 2H). MASS (m/z): 379(M$^+$).

REFERENCE EXAMPLE 4

4-[2-(3,5-Dichloro-4-pyridyl)ethyl]-7-methoxybenzofuran-2-carboxylic Acid (Compound N)

(Step 1): Ethyl 4-[2-(3,5-Dichloro-4-pyridyl)ethyl]-7-methoxybenzofuran-2-carboxylate Ethyl 4-[2-(3,5-dichloro-4-pyridyl)-1-oxoethyl]-7-methoxybenzofuran-2-carboxylate (3.0 g) obtained in Reference Example 3 was dissolved in anhydrous dichloromethane (150 ml), a boron trifluoride ethyl ether complex (4.5 ml) and triethylsilane (8.8 ml) were added thereto at −78° C., and the mixture was returned to room temperature and stirred overnight. 1 N aqueous HCl was added thereto, and the reaction mixture was extracted with chloroform. The extract was washed with 1 N aqueous HCl and then with a saturated aqueous sodium chloride solution and dried over sodium sulfate, and the solvent was distilled off under reduced pressure. The residue was purified by silica gel column chromatography (hexane:ethyl acetate=3:2) and recrystallized from ethanol to give the desired compound (2.0 g, 69%) as colorless crystals.

$^1$H-NMR(CDCl$_1$, δ ppm): 1.43 (t, J=7 Hz, 3H), 3.02–3.08 (m, 2H), 3.21–3.27 (m, 2H), 4.01 (s, 3H), 4.45 (q, J=7 Hz, 2H), 6.84 (d, J=8 Hz, 1H), 7.01 (d, J=8 Hz, 1H), 7.60 (s, 1H), 8.45 (s, 2H). MASS (m/z): 393(M$^+$).

(Step 2): Compound N

Ethyl 4-[2-(3,5-dichloro-4-pyridyl)ethyl]-7-methoxybenzofuran-2-carboxylate (1.9 g) was dissolved in dioxane (20 ml)-methanol (5 ml), and 1 N aqueous NaOH (15 ml) as added thereto. The mixture was returned to room temperature and stirred for 30 minutes. After 1 N aqueous HCl was dropwise added thereto under cooling on ice, the precipitated crystals were collected by filtration and washed with water to give Compound N (1.72 g, 97%) as colorless crystals.

$^1$H-NMR(DMSO-d$_6$, δ ppm): 3.17–3.25 (m, 4H), 3.91 (s, 3H), 6.97 (s, 2H), 7.58 (s, 1H), 8.56 (s, 2H). MASS (m/z): 365(M$^+$).

REFERENCE EXAMPLE 5

4-[2-(3,5-Dichloro-4-pyridyl)-1-oxoethyl]-2-(1-piperazinyl)carbonyl-7-methoxybenzofuran (Compound O)

Compound M (4.12 g) obtained in Reference Example 3 was dissolved in DMF (150 ml), 1-hydroxybenzotriazole monohydrate (5.8 g) and N-ethyl-N-'3-dimethylaminopropylcarbodiimide monohydrochloride (8.2 g) were added thereto, and the mixture was stirred at room temperature for 10 minutes. The mixture was dropwise added to a solution of piperazine (18.6 g) in DMF (300 ml) and the mixture was stirred at room temperature for 12 hours. The solvent was distilled off under reduced pressure and the residue was extracted with chloroform. The extract was washed a saturated aqueous sodium chloride solution and dried over sodium sulfate, and the solvent was distilled off. The resulting residue was suspended in ethanol and the precipitated crystals were collected by filtration to give the desired compound (3.54 g, 73%) as colorless crystals.

$^1$H-NMR(CDCl$_3$, δ ppm): 2.88–2.96 (m, 4H), 3.73–3.81 (m, 4H), 4.12 (s, 3H), 4.73 (s, 2H), 6.95 (d, J=8 Hz, 1H), 7.86 (s, 1H), 8.02 (d, J=8 Hz, 1H), 8.53 (s, 1H). MASS (m/z): 447(M$^+$).

INDUSTRIAL APPLICABILITY

According to the present invention, there are provided benzofuran derivatives which have phosphodiesterase (PDE) IV inhibitory activity, and which are useful as a therapeutic agent for inflammatory allergic diseases such as bronchial asthma, allergic rhinitis and nephritis; autoimmune diseases such as rheumatism, multiple sclerosis, Crohn's diseases, psoriasis and systemic lupus erythematosus; diseases of the central nervous system such as depression, amnesia and dementia; organopathy associated with ischemic reflux caused by cardiac failure, shock and cerebrovascular disease, and the like; insulin-resistant diabetes; wounds; AIDS; and the like, without causing vomiting as a side effect.

What is claimed is:

1. A compound represented by formula (I):

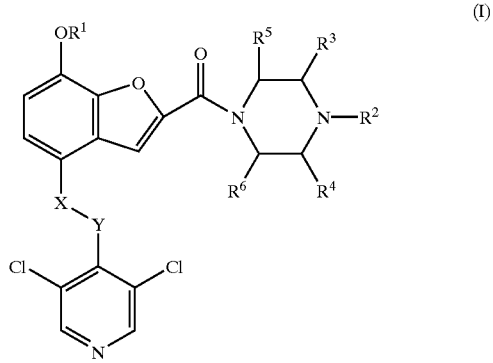

wherein R$^1$ represents C1–8 alkyl,

R$^2$ represents hydrogen, C1–8 alkyl, or C1–8 alkyl substituted with 1 to 3 substituents independently selected from the group consisting of hydroxy, C1–8 alkoxy and C1–8 alkoxy substituted with the same or different 1 to 3 hydroxy, involving C1–8 chains, R$^3$, R$^4$, R$^5$ and R$^6$ independently represent hydrogen or lower alkyl, X represents CH$_2$, or C=O, and Y represents CH$_2$ or NH or a pharmaceutically acceptable salt thereof.

2. The compound or a pharmaceutically acceptable salt thereof according to claim 1, wherein R$^2$ is C1–8 alkyl, or C1–8 alkyl substituted with the same or different 1 to 3 substituents independently selected from the group consisting of hydroxy, C1–8 alkoxy and C1–8 alkoxy substituted with the same or different 1 to 3 hydroxy involving C1–8 chains.

3. The compound or a pharmaceutically acceptable salt thereof according to claim 1, wherein R$^2$ is C1–8 alkyl substituted with hydroxy.

4. The compound or a pharmaceutically acceptable salt thereof according to claim 1, wherein X is CH$_2$, and Y is CH$_2$; or X is C=O, and Y is CH$_2$ or NH.

5. The compound or a pharmaceutically acceptable salt thereof according to claim 4, wherein X is CH$_2$, and Y is CH$_2$; or X is C=O, and Y is CH$_2$.

6. The compound or a pharmaceutically acceptable salt thereof according to claim 4, wherein X is C=O, and Y is NH.

7. A pharmaceutical composition which comprises the compound according to claim 1 or a pharmaceutically acceptable salt thereof as an active ingredient and a pharmaceutically acceptable carrier.

8. A method for treating inflammatory allergic diseases, which comprises administering an effective amount of the compound according to claim 1 or a pharmaceutically acceptable salt thereof and a pharmaceutically acceptable carrier.

* * * * *

UNITED STATES PATENT AND TRADEMARK OFFICE
CERTIFICATE OF CORRECTION

PATENT NO. : 6,395,738 B1
DATED : May 28, 2002
INVENTOR(S) : Etsuo Ohshima et al.

It is certified that error appears in the above-identified patent and that said Letters Patent is hereby corrected as shown below:

Title page,
Item [56], OTHER PUBLICATIONS, "The Journal of Investigative Dermotalogy," should read -- The Journal of Investigative Dermatology, --.

Column 2,
Line 63, "ethyl,.propyl," should read -- ethyl, propyl, --.

Column 10,
Line 1, "(in" should read -- (In --.

Column 11,
Line 38, "above." should read -- above.) --.

Column 14,
Line 38, "phsysiological" should read -- physiological --;
Line 43, "a" should be deleted;
Line 49, "assay.(ELISA)." should read -- assay (ELISA). --; and
Line 66, "Ltd.)" should read -- Ltd.). --.

Column 17,
Line 25, "desired" should read -- desirable --.

Column 19,
Line 56, "cm⁻):" should read -- $cm^{-1}$): --.

Column 20,
Line 9, "(M⁻);" should read -- $(M^+)$; --; and "cm⁺¹):" should read -- $cm^{-1}$): --.

Column 27,
Line 3, "cm⁻):" should read -- $cm^{-1}$): --.

UNITED STATES PATENT AND TRADEMARK OFFICE
CERTIFICATE OF CORRECTION

PATENT NO. : 6,395,738 B1
DATED : May 28, 2002
INVENTOR(S) : Etsuo Ohshima et al.

It is certified that error appears in the above-identified patent and that said Letters Patent is hereby corrected as shown below:

Column 31,
Line 66, "washed" should read -- washed with --.

Signed and Sealed this

First Day of July, 2003

JAMES E. ROGAN
*Director of the United States Patent and Trademark Office*